United States Patent
Somerville et al.

(10) Patent No.: US 6,291,742 B1
(45) Date of Patent: Sep. 18, 2001

(54) PRODUCTION OF HYDROXYLATED FATTY ACIDS IN GENETICALLY MODIFIED PLANTS

(75) Inventors: Chris Somerville, Portola Valley; Pierre Broun, Burlingame, both of CA (US); Frank van de Loo, Lexington, KY (US)

(73) Assignees: Carnegie Institution of Washington, Washington, DC (US); Monsanto Company Inc., St. Louis, MO (US)

(*) Notice: Subject to any disclaimer, the term of this patent is extended or adjusted under 35 U.S.C. 154(b) by 0 days.

(21) Appl. No.: 08/530,862

(22) Filed: Sep. 20, 1995

Related U.S. Application Data

(63) Continuation-in-part of application No. 08/320,982, filed on Oct. 11, 1994, now Pat. No. 5,801,026, which is a continuation-in-part of application No. 08/314,596, filed on Sep. 26, 1994, now Pat. No. 5,668,292.

(51) Int. Cl.$^7$ .............................. A01H 5/00; C12N 15/82
(52) U.S. Cl. .......................... 800/281; 800/298; 435/468
(58) Field of Search .................................. 800/205, 250, 800/281, 298; 435/69.1, 172.3, 240.4, 468; 536/23.6

(56) References Cited

FOREIGN PATENT DOCUMENTS

| | | |
|---|---|---|
| WO9411516 | 5/1994 | (WO) . |
| WO9418337 | 8/1994 | (WO) . |
| WO9610075 | 4/1996 | (WO) . |
| WO9721340 | 6/1997 | (WO) . |

OTHER PUBLICATIONS

Van De Loo et al., "An oleate 12–hydroxylase from Ricinus comunis L. is a fatty acyl saturase homolog", Proc. Natl. Acad. Sci. USA, Jul. 18, 1995; 92(15):6743–7.

Shanklin et al., "Eight histidine residues are ctalyticaly essential in a membrane–associated iron enzyme, stearoyl––CoA desaturase, and are conserved in alkane hydroxylase and xylene monooxygenase", Biochemistry, US, American Chemical Society, No. 33, Jan. 1, 1994; 12787–12794.

Broun et al., "Accumulation of ricinoleic, lesquerolic, and densipolic acids in seeds of transgenic Arabidopsis plants that express a fatty acyl hydroxylase cDNA from caster bena", Plant Physiology, US, American Society of Plant Physiologists, vol. 113, No. 113, 1997, pp 933–942.

Broun et al., "A bifunctional oleate 12–hydroxylase: desaturase from Lesquerella fendleri", Plant Journal, GB, Blackwell Scientific Publications, vol. 13, No. 2, Feb. 1, 1998, pp 201–210.

Broun et al., "Catalytic plasticity of fatty acid modification enzymes underlying chemical diversity of plant lipids", Science, US American Assoc; For The Advancement of Science, vol. 282, No. 282, Nov. 13, 1998, pp 1315–1317.

Griffiths et al., "Delta6 and Delta12–Desaturase Activities and Phosphatidic Acid Formation In Microsomal Preparations From The Devloping Cotyledons of Common Borage", Biochemical Journal, vol. 252, No. 3, pp. 641–647, Jun. 15, 1988.

Van de Loo et al., "An Oleate 12–Hydroxylase From Ricinus Communis L. is a fatty acyl desaturase homolog", Proceeding of the National Academy of Sciences, vol. 92, pp. 6743–0647, Jul. 1995.

Database MBL Nucleotide and Protein Sequences, Apr. 16, 1995, XP002120959, Lycopersicum esculentum.

Altschul et al, J. Mol. Biol., 215:403–410 (1990).
Arondel et al, Science, 258:1353–1355 (1992).
Atsmon et al, Castor, McGraw–Hill, New York pp. 438–447 (1989).
Bafor et al, Biochem., 280:507–514 (1991).
Battey et al, Plant Physiol., 90:835–840 (1989).
Bechtold et al, C.R. Acad. Sci. Paris, 316:1194–1199 (1993).
Beltz et al, Methods in Enzymology, 100:266–285 (1983).
Bray et al, Planta, 172:364–370 (1987).
Browse et al, Ann. Rev. Plant Physiol. Plant Mol. Biol., 42:467–506 (1991).
Canvin, Can. J. Biochem. Physiol., 41:1879–1885 (1963).
Ditta et al, Proc. Natl. Acad. Sci. USA, 77:7347–7351 (1980).
Fox et al, Proc. Natl. Acad. Sci., 90:2486–2490 (1993).
Galliard et al, J. Biol. Chem., 241:5806–5812 (1966).
Gould et al, Proc. Natl. Acad. Sci. USA, 86:1934–1938 (1989).
Greenwood et al, Can. J. Bot., 60:1751–1760 (1982).
Gunstone et al, The Lipid Handbook, Chapman and Hall, London, Chapters 1.9, pp. 19–20 and 3.3.5, pp. 57–58 (1986).
Howling et al, Biochim. Biophys. Acta, 260:10–19 (1972).
Huyuh t al, DNA Cloning, vol. 1: A Practical Approach, (ed) D.M. Glover, IRL Press, Washington, D.C., pp. 49–77 (1985).
Iba et al, J. Biol. Chem., 268:24099–24105 (1993).
James et al, Biochem. J., 95:448–452 (1965).
Kearns et al, Arch. Biochem. Biophys., 284:431–436 (1991).
Knuzton et al, Proc. Natl. Acad. Sci. USA, 89:2624–2628 (1992).
Kok et al, J. Biol. Chem., 264:5435–5441 (1989).
Konez et al, Mol. Gen. Genet., 204:383–396 (1986).
Kren et al, Experentia, 41:1476–1477 (1985).
Miquel et al, J. Biol. Chem., 267:1502–1509 (1992).

(List continued on next page.)

Primary Examiner—Elizabeth F. McElwain
(74) Attorney, Agent, or Firm—Pillsbury Winthrop LLP

(57) ABSTRACT

This invention relates to plant fatty acyl hydroxylases. Methods to use conserved amino acid or nucleotide sequences to obtain plant fatty acyl hydroxylases are described. Also described is the use of cDNA clones encoding a plant hydroxylase to produce a family of hydroxylated fatty acids in transgenic plants.

22 Claims, 18 Drawing Sheets

OTHER PUBLICATIONS

Moreau et al, Plant Physiol., 67:672–676 (1981).
Morris, Biochem. Biophys. Res. Commun., 29:311–315 (1967).
Morris, Biochem. J., 118:681–693 (1970).
Morris et al, Biochem. J., 100:29c–30c (1966).
Newman et al, Plant Cell, 5:701–714 (1993).
Okuley et al, Plant Cell, 6:147–158 (1994).
Ooms et al, Plasmid, 7:15–29 (1982).
Panaccione et al, Gene, 86:163–170 (1990).
Prasad et al. J. Am. Oil Chem. Soc., 64:1424–1427 (1987).
Puissant et al. BioTechniques, 8:148–149 (1990).
Sambrook et al, Molecular Cloning: a Laboratory Manual, 2n ed., Cold Spring Harbor Laboratory Press (1989).
Schmidt et al, American Society of Plant Physiologists, pp. 40–49 (1993).
Smith, Fatty Acids, Pryde E.H., Ed., American Oil Chemists' Society, Champaign, 2nd ed., pp. 29–47.
Smith et al, Biochem. J., 287:141–144 (1992).
Suzuki et al, J. Bacteriol., 173:1690–1695 (1991).
Thiede et al, J. Biol. Chem., 261:13230–13235 (1986).
van de Loo et al, Lipid Metabolism in Plants, T.S. Moore Jr., Ed., CRC Press, Boca Raton, pp. 91–126 (1993).
van de Loo et al, Plant Physiol., 105:443–444 (1994).
von Heijne, J. Mol. Biol., 184:99–105 (1985).
Yadav et al, Plant Physiol., 103:467–476 (1993).
Arondel et al., *Science* 258:1353–1355 (1992).
Shanklin et al., *Biochemistry* 33:12787–12794 (1994).
Gibson et al., *Plant Physiol.* 106:1615–1621 (1994).
Matzke et al., *Plant Physiol.* 107:679–685 (1995).
Topfer et al., *Science* 268:681–686 (1995).
Murray et al, Rapid isolation of high molecular wight plant DNA, Nucleic Acids Research, vol. 8 No. 19 1980, pp. 4321–4325.
Carlson et al., "Analysis of Oil and Meat from *Lesquerella fendlier* Seed,"JAOCS, vol. 67, No. 7 (Jul. 1990), pp. 438–442.
van de Loo et al., "An oleate 12–hydroxylase from *Ricinus communis* L. is a fatty acyl desaturase homolog," Proc. Natl. Acad. Sci. USA 92 (1995), pp. 6743–6747.
Jones et al., "Effective vectors for transformation, expression of heterologous genes, and assaying transposon excision in transgenic plants," Transgenic Research 1, 285–297 (1992).

LON #1: MASS 187
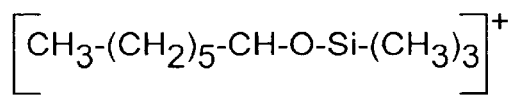
LON #2: MASS 299
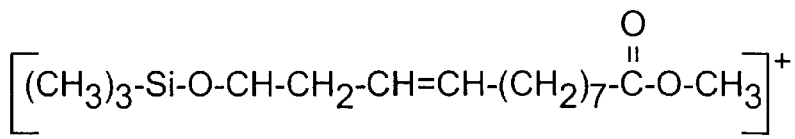
LON #3: MASS 270 (CHARACTERISTIC REARRANGEMENT ION)
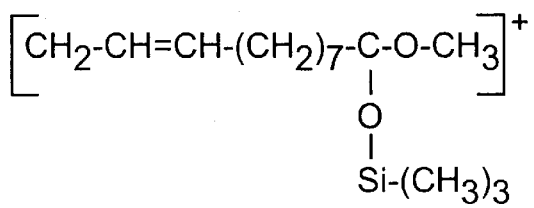
LON #4: MASS 185 (DESATURATED ANALOG OF LON #1)
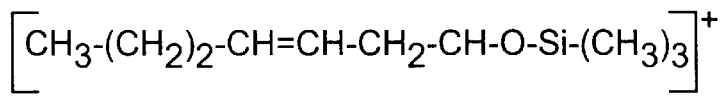
LON #5: MASS 298 (ELONGATED ANALOG OF LON #3)
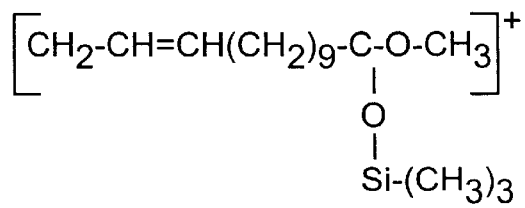
LON #6: MASS 327 (ELONGATED ANALOG OF ION)
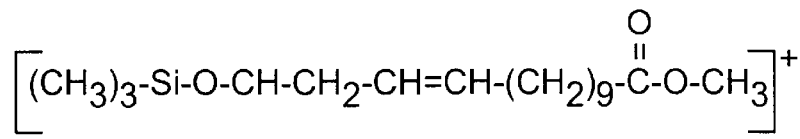
*FIG. 2*

```
        1                  20                  30                  40                  50                  60
TATTGGCACC  GGCGGCACCA  TTCCAACAAT  GGATCCCCTAG  AAAAAGATGA  AGTCTTTGTC
        70                  80                  90                 100                 110                 120
CCACCTAAGA  AAGCTGCAGT  CANATGGTAT  GTCAAATACC  TCAACAACCC  TCTTGGACGC
       130                 140                 150                 160                 170                 180
ATTCTGGTGT  TAACAGTTCA  GTTTATCCTC  GGGTGGCCTT  TGTATCTAGC  CTTTAATGTA
       190                 200                 210                 220                 230                 240
TCAGGTAGAC  CTTATGATGG  TTTCGCTTCA  CATTTCTTCC  CTCATGCACC  TATCTTTAAG
       250                 260                 270                 280                 290                 300
GACCGTGAAC  GTCTCCAGAT  ATACATCTCA  GATGCTGGTA  TTCTAGCTGT  CTGTTATGGT
       310                 320                 330                 340                 350                 360
CTTTACCGTT  ACGCTGCTTC  ACAAGGATTG  ACTGCTATGA  TCTGCGTCTA  CGGAGTACCG
       370                 380                 390                 400                 410                 420
CTTTTGATAG  TGAACTTTTT  CCTTGTCTTG  GTCACTTTCT  TGCAGCACAC  TCATCCTTCA
       430                 440                 450                 460                 470                 480
TTACCTCACT  ATGATTCAAC  CGAGTGGGAA  TGGATTAGAG  GAGCTTTGGT  TACGGTAGAC
       490                 500                 510                 520                 530                 540
AGAGACTATG  GAATCTTGAA  CAAGGTGTTT  CACAACATAA  CAGACACCCA  CGTAGCACAC
       550
CAC
```

*FIG. 5*

```
  1 TATAGGCACC GGAGGCACCA TTCCAACACA GGATCCCTCG AAAGAGATGA AGTATTTGTC
 61 CCAAAGCAGA AATCCGCAAT CAAGTGGTAC GGCGAATACC TCAACAACCC TCCTGGTCGC
121 ATCATGATGT TAACTGTCCA GTTCGTCCTC GGATGGCCCT TGTACTTAGC CTTCAACGTT
181 TCTGGCAGAC CCTACAATGG TTTCGCTTCC CATTTCTTCC CCAATGCTCC TATCTACAAC
241 GACCGTGAAC GCCTCCAGAT TTACATCTCT GATGCTGGTA TCTGTCTAAA CTGTTATGGT
301 CTTTACCGTT ACGCTGTTGC ACAAGGACTA GCCTCAATGA ATCACTTACT CGGAGTTCCG
361 CTTCTGATAG TTAACTTTTT CCTCGTCTTG GCCTCAATGA ATCACTTACT CGGAGTTCCG
361 CTTCTGATAG TTAACTTTTT CCTCGTCTTG ATCACTTACT TACAACACAC TCACCCTGCG
421 TTGCCTCACT ATGATTCATC AGAGTGGGAT TGGCTTAGAG GAGCTTTAGC TACTGTAGAC
481 AGAGACTATG GAATCTTGAA CAAGGTGTTC CATAACATCA CAGACACCCA CGTCGCACAC
541 CACT
```

FIG. 6

| | | | | | | | | | | | | | | | |
|---|---|---|---|---|---|---|---|---|---|---|---|---|---|---|---|
| AT | GAA | GCT | TTA | TAA | GAA | GTT | TTT | AGT | CTC | TGG | CAG | AGA | AAT | TNT | 47 |
| GCT | AAT | TGG | TAG | TGA | CAG | TTG | CAA | AAG | TGG | GAA | TGA | CAG | GGA | TGG | 95 |
| GTG | NTG | ATG | CTG | ATG | TGG | CTG | TTT | TGT | CAT | CAA | ATA | AAT | TTG | ACT | 143 |
| ACA | TTA | CTT | GTT | GCT | GCC | TAC | TCC | TTC | TAT | GAA | CTA | CGC | CCA | TTT | 191 |
| TGG | ACC | CAC | GAN | CCT | TCC | ATT | CTC | TAA | ACC | CTC | CGT | GCT | CAC | CAG | 239 |
| AAG | AGA | AGC | CAA | GAG | AGA | AGA | AAT | AGA | AGT | GAG | TCT | CGT | AGG | ATT | 287 |
| TTC | TTC | ATC | GTT | ATT | AAC | GTA | CTT | AGT | TTT | TGA | GTT | CTG | CTC | ATA | 335 |
| ATC | TAG | TAC | ATG | CAA | TAG | ATT | GAC | AAT | TGT | TCC | CCA | TTC | ATA | TGA | 383 |
| | | | | | | Met | Gly | Ala | Gly | Arg | Arg | Ile | Met | Val | Thr | 10 |
| CAG | CTT | GAA | TTC | AAG | ATG | GGT | GCT | GGT | GGA | AGA | ATA | ATG | GTT | ACC | 431 |
| Pro | Ser | Ser | Lys | Lys | Ser | Glu | Thr | Glu | Ala | Leu | Lys | Arg | Gly | Pro | Cys | 26 |
| CCC | TCT | TCC | AAG | AAA | TCA | GAA | ACT | GAA | GCC | CTA | AAA | CGT | GGA | CCA | TGT | 479 |
| Glu | Lys | Pro | Pro | Phe | Thr | Val | Lys | Asp | Leu | Lys | Lys | Ala | ILe | Pro | Gln | 42 |
| GAG | AAA | CCA | CCA | TTC | ACT | GTT | AAA | GAT | CTG | AAG | AAA | GCA | ATC | CCA | CAG | 527 |

FIG. 8A (CONT-1)

| | | | | | | | | | | | | | | | | | |
|---|---|---|---|---|---|---|---|---|---|---|---|---|---|---|---|---|---|
| His CAT | Cys TGT | Phe TTC | Lys AAG | Arg CGC | Ser TCT | Ile ATC | Pro CCT | Arg CGT | Ser TCT | Phe TTC | Ser TCC | Tyr TAC | Leu CTT | Leu CTC | Thr ACA | 58 | 575 |
| Asp GAT | Ile ATC | Thr ACT | Leu TTA | Val GTT | Ser TCT | Cys TGC | Phe TTC | Tyr TAC | Tyr TAC | Val GTT | Ala GCC | Thr ACA | Asn AAT | Tyr TAC | Phe TTC | 74 | 623 |
| Ser TCT | Leu CTT | Leu CTT | Pro CCT | Gln CAG | Gly GGC | Pro CCT | Phe TTC | Tyr TAC | Tyr TAC | Leu CTA | Ala GCT | Trp TGG | Pro CCT | Leu CTC | Tyr TAT | 90 | 671 |
| Trp TGG | Val GTA | Cys TGT | Gln CAA | Gly GGC | Gly GGT | Val GTC | Cys TGT | Gly GGT | Leu TTA | Ile ATC | Trp TGG | Val GTC | Ile ATT | Gly GGC | His CAT | 106 | 719 |
| Glu GAA | Cys TGT | Gly GGT | His CAC | His CAT | Ala GCA | Phe TTC | Ser AGT | Tyr TAT | Gln CAA | Trp TGG | Val GTA | Asp GAT | Val GTA | Tyr TAC | Thr ACT | 122 | 767 |
| Val GTT | Gly GGT | Phe TTT | Ile ATC | Phe TTC | Arg CGT | Ser TCC | Leu CTT | Asp GAC | Tyr TAT | Pro CCT | Gly GGA | Asn AAT | Val GTC | Asp GAC | Thr ACT | 138 | 815 |
| Lys AAA | Tyr TAC | Ser AGT | His CAT | Phe TTC | Lys AAG | His CAT | Pro CCG | Ser TCC | Lys AAA | Tyr TAC | Val GTC | Ala GCA | Gly GGA | Lys AAA | Trp TGG | 154 | 863 |
| Asp GAT | Glu GAA | Val GTC | Phe TTT | Val GTC | Pro CCA | Arg CGT | Pro CCG | Ile ATT | Gly GGA | Arg CGC | Ala GCT | Leu CTC | Tyr TAT | Trp TGG | Val GTT | 170 | 911 |
| Lys AAA | Tyr TAC | Leu CTC | Asn AAC | Asn AAC | Pro CCT | Leu CTT | Gly GGA | Arg CGC | Ile ATT | Leu CTG | Val GTG | Leu TTA | Thr ACA | Val GTT | Gln CAG | 186 | 959 |

| | | | | | | | | | | | | | | | | |
|---|---|---|---|---|---|---|---|---|---|---|---|---|---|---|---|---|
| Phe | Ile | Leu | Gly | Trp | Pro | Leu | Tyr | Leu | Ala | Phe | Asn | Val | Ser | Gly | Arg | 202 |
| TTT | ATC | CTC | GGG | TGG | CCT | TTG | TAT | CTA | GCC | TTT | AAT | GTA | TCA | GGT | AGA | 1007 |
| Pro | Tyr | Asp | Gly | Phe | Ala | Ser | His | Phe | Phe | Pro | His | Ala | Pro | Ile | Phe | 218 |
| CCT | TAT | GAT | GGT | TTC | GCT | TCA | CAT | TTC | TTC | CCT | CAT | GCA | CCT | ATC | TTT | 1055 |
| Lys | Asp | Arg | Glu | Arg | Leu | Leu | Ile | Ile | Ser | Asp | Ala | Ala | Pro | Ile | Leu | 234 |
| AAA | GAC | CGA | GAA | CGC | CTC | CTC | ATA | ATC | TCA | GAT | GCT | GCA | CCT | ATT | CTA | 1103 |
| Ala | Val | Cys | Tyr | Gly | Leu | Gln | Arg | Tyr | Ala | Ser | Gln | Ala | Gly | Ile | Thr | 250 |
| GCT | GTC | TGT | TAT | GGT | CTT | CAG | CGT | TAC | GCT | GAT | CAA | GCT | GGT | ATT | ACT | 1151 |
| Ala | Met | Ile | Cys | Val | Tyr | Tyr | Pro | Gly | Val | Ile | Leu | Val | Gly | Leu | Phe | 266 |
| GCT | ATG | ATC | TGC | GTA | TAC | TAC | CCG | GGA | GTA | ATA | TTG | GTG | GGA | TTG | TTC | 1199 |
| Leu | Val | Leu | Thr | Thr | Phe | Leu | Gln | His | Thr | Leu | Pro | Ser | Asn | Leu | Thr | 282 |
| CTT | GTC | TTG | ACC | ACT | TTC | TTG | CAG | CAC | ACT | TTG | CCT | TCG | AAC | TTA | ACT | 1247 |
| Tyr | Asp | Ser | Thr | Glu | Trp | Trp | Asn | Ile | Arg | Gly | Ala | His | Phe | Pro | Phe | 298 |
| TAT | GAT | TCA | ACC | GAG | TGG | TGG | AAC | ATT | AGA | GGA | GCT | CAT | TTC | CCT | TTC | 1295 |
| Asp | Arg | Asp | Tyr | Gly | Tyr | Val | Lys | Ala | Val | Thr | Thr | Ile | Thr | Thr | Val | 314 |
| GAC | AGA | GAC | TAT | GGA | TAT | GTG | AAG | GCA | GTG | ACG | ACA | ATA | ACA | ACA | GTA | 1343 |
| Thr | His | Val | Ala | His | Leu | Phe | His | Ile | Pro | His | Tyr | Asn | Asp | Ala | 330 |
| ACA | CAT | GTG | GCT | CAT | CTC | TTT | CAT | ATA | CCG | CAT | TAT | AAC | GAC | GCA | 1391 |

| | | | | | | | | | | | | |
|---|---|---|---|---|---|---|---|---|---|---|---|---|
| Met<br>ATG | Glu<br>GAA | Ala<br>GCT | Thr<br>ACA | Glu<br>GAG | Ala<br>GCG | Ile<br>ATA | Lys<br>AAG | Pro<br>CCA | Ile<br>ATA | Leu<br>CTT | Gly<br>GGT | Asp<br>GAT | Tyr<br>TAC | Tyr<br>TAC | His<br>CAC | 346<br>1439 |
| Phe<br>TTC | Asp<br>GAT | Gly<br>GGA | Thr<br>ACA | Pro<br>CCG | Trp<br>TGG | Tyr<br>TAT | Val<br>GTG | Ala<br>GCC | Met<br>ATG | Tyr<br>TAT | Arg<br>AGG | Glu<br>GAA | Ala<br>GCA | Lys<br>AAG | Glu<br>GAG | 362<br>1487 |
| Cys<br>TGT | Leu<br>CTC | Tyr<br>TAT | Val<br>GTA | Glu<br>GAA | Pro<br>CCG | Asp<br>GAT | Thr<br>ACG | Arg<br>CGT | Gly<br>GGG | Lys<br>AAG | Lys<br>AAA | Gly<br>GGT | Val<br>GTC | Tyr<br>TAC | 378<br>1535 |
| Tyr<br>TAT | Asn<br>AAC | Asn<br>AAT | Lys<br>AAG | Leu<br>TTA | Leu<br>TTA | TGA | GGC | GAG | AGA | AGT | GCA | ATT | 384<br>1583 |
| ATC | AAT | CTT | CAT | TTC | CAT | GTT | TAG | GGC | TTT | AAG | AAG | CTA | TGC | | | 1631 |
| TTT | GTT | TCA | ATA | ATC | TCA | GAG | GGT | GTC | TTG | TGT | TCT | GGT | GCA | TTT | | 1679 |
| TGC | CTA | GTT | ATG | TGG | TCC | AAG | ATN | TAG | TTC | AAA | CTT | CCT | GCT | | | 1727 |
| GTG | CTG | CCC | AGT | GAA | TGT | GAA | TTA | GTG | TTT | AAA | ATA | CTC | GGA | ACG | | 1775 |
| AAT | TGA | CCA | CAA | NAT | ATC | AAC | CGG | CTA | TCC | GAA | TTC | CAT | ATC | CGA | | 1823 |
| AAA | CCG | GAT | ATC | CAA | ATT | TCC | AGA | GTA | CTT | AG | | | | | | 1855 |

```
              10         20         30         40         50
LFFAH12    1  MGAGGRIM-- --VTPSSKKS --ETEALKRG PCEKPPFTVK DLKKAIPQHC
FAH12      1  MGGGGRMSTV ITSNNSEKKG --GSSHLKRA PHTKPPFTLG DLKRAIPPHC
ATFAD2     1  MGAGGRMP-- --VPTSSKKS --ETDTTKRV PCEKPPFSVG DLKKAIPPHC
BNFAD2     1  MGAGGRMQ-- --VSPPSKKS --ETDNIKRV PCETPPFTVG ELKKAIPPHC
GMFAD2-1   1  MGLA-KETTM GGRGRVAKVE VQGKKPLSRV PNTKPPFTVG QLKKAIPPHC
GMFAD2-2   1  MGAGGR---- TDVPPANRKS --EVDPLKRV PFEKPQFSLS QIKKAIPPHC
ZMFAD2     1  MGAGGRMTEK EREKQEQLAR ATGGAAMQRS PVEKPPFTLG QIKKAIPPHC
RCFAD2     1  ---------- ---------- ---------- ---------- ----------

60         70         80         90        100
LFFAH12   51  FKRSIPRSFS YLLTDITLVS CFYYVATNYF SLLPQPLSTY LAWPLYWVCQ
FAH12     51  FERSFVRSFS YVAYDVCLSF LFYSIATNFF PYISSPLS-Y VAWLVYWLFQ
ATFAD2    51  FKRSIPRSFS YLISDIIIAS CFYYVATNYF SLLPQPLS-Y LAWPLYWACQ
BNFAD2    51  FKRSIPRSFS HLIWDIIIAS CFYYVATTYF PLLPNPLS-Y FAWPLYWACQ
GMFAD2-1  51  FQRSLLTSFS YVVYDLSFAF IFY-IATTYF HLLPQFS-L  IAWPIYWVLQ
GMFAD2-2  51  FQRSVLRSFS YVVYDLTIAF CLYYVATHYF HLLPGPLS-F RGMAIYWAVQ
ZMFAD2    51  FERSVLKSFS YVVHDLVIAA ALLYFALAII PALPSPLR-Y AAWPLYWIAQ
RCFAD2     1  ---------- ---------- ---------- ---------- ----------

110        120        130        140        150
LFFAH12  101  GCVLTGIWVI GHECGHHAFS DYQWVDDTVG FIFHSFLLVP YFSWKYSHRR
FAH12    101  GCILTGLWVI GHECGHHAFS EYQLADDIVG LIVHSALLVP YFSWKYSHRR
ATFAD2   101  GCVLTGIWVI AHECGHHAFS DYQWLDDTVG LIFHSFLLVP YFSWKYSHRR
BNFAD2   101  GCVLTGVWVI AHECGHAAFS DYQWLDDTVG LIFHSFLLVP YFSWKYSHRR
GMFAD2-1 101  GCLLTGVWVI AHECGHHAFS KYQWVDDVVG LTLHSTLLVP YFSWKISHRR
GMFAD2-2 101  GCILTGVWVI AHECGHHAFS DYQLLDDIVG LILHSALLVP YFSWKYSHRR
ZMFAD2   101  G--------- -----AFS   DYSLLDDVVG LVLHSSLMVP YFSWKYSHRR
RCFAD2     1  -------WVM AHDCGHHAFS DYQLLDDVVG LILHSCLLVP YFSWKHSHRR
```

```
LFFAH12   151 HHSNNGSLEK DEVFVPPKKA AVKWYVKYL- NNPLGRILVL TVQFILGWPL 200
FAH12     151 HHSNIGSLER DEVFVPKSKS KISWYSKYS- NNPPGRVLTL AATLLLGWPL 200
ATFAD2    151 HHSNTGSLER DEVFVPKQKS AIKWYGKYL- NNPLGRIMML TVQFVLGWPL 200
BNFAD2    151 HHSNTGSLER DEVFVPR-RS QTSSGTAST- STTFGRTVML TVQFTLGWPL 200
GMFAD2-1  151 HHSNTGSLDR DEVFVPKPKS KVAWFSKYL- NNPLGRAVSL LVTLTIGWPM 200
GMFAD2-2  151 HHSNTGSLER DEVFVPKQKS CIKWYSKYL- NNPPGRVLTL AVTLTLGWPL 200
ZMFAD2    151 HHSNTGSLER DEVFVPKKKE ALPWYTPVY  NNPVGRVVHI VVQLTLGWPL 200
RCFAD2    151 HHSNTGSLER DEVFVPKKKS SIRWYSKYL- NNPPGRIMTI AVTLSLGWPL 200

LFFAH12   201 YLAFNVSGRP YDG-FASHFF PHAPIFKDRE RLQIYISDAG ILAVCYGLYR 250
FAH12     201 YLAFNVSGRP YDR-FACHYD PYGPIFSERE RLQIYIADLG IFATTFVLYQ 250
ATFAD2    201 YLAFNVSGRP YDG-FACHFF PNAPIYNDRE RLQIYLSDAG ILAVCFGLYR 250
BNFAD2    201 YLAFNVSGRP YDGGFACHFH PNAPIYNDRE RLQIYISDAG ILAVCYGLLP 250
GMFAD2-1  201 YLAFNVSGRP YDS-FASHYH PYAPIYSNRE RLLIYVSDVA LFSVTYSLYR 250
GMFAD2-2  201 YLALNVSGRP YDR-FACHYD PYGPIYSDRE RLQIYISDAG VLAVVYGLFR 250
ZMFAD2    201 YLATNASGRP YPR-FACHFD PYGPIYNDRE RAQIFVSDAG VVAVAFGLYK 250
RCFAD2    201 YLAFNVSGRP YPR-FACHYD PYGPIYNDRE RIEIFISDAG VLAVTFGLYQ 250
```

```
                    260         270         280         290         300
LFFAH12   251  YAASQGLTAM  ICVYGVPLLI  VNFFLVLVTF  LQHTHPSLPH  YDSTEWEWIR  300
FAH12     251  ATMAKGLAWV  MRIYGVPLLI  VNCFLVMITY  LQHTHPAIPR  YGSSEWDWLR  300
ATFAD2    251  YAAAQGMASM  ICLYGVPLLI  VNAFLVLITY  LQHTHPSLPH  YDSSEWDWLR  300
BNFAD2    251  YAAVQGVASM  VCFLRVPLLI  VNGFLVLITY  LQHTHPSLPH  YDSSEWDWLR  300
GMFAD2-1  251  VATLKGLVWL  LCVYGVPLLI  VNGFLVTITY  LQHTHFALPH  YDSSEWDWLK  300
GMFAD2-2  251  LAMAKGLAWV  VCVYGVPLLV  VNGFLVLITF  LQHTHPALPH  YTSSEWDWLR  300
ZMFAD2    251  LAAAFGVWWV  VRVYAVPLLI  VNAWLVLITY  LQHTHPSLPH  YDSSEWDWLR  300
RCFAD2    251  LAIAKGLAWV  VCVYGVPLLV  VNSFLVLITF  LQHTHPALPH  YDSSEWDWLR  300

310         320         330         340         350
LFFAH12   301  GALVTVDRDY  GILNKVFHNI  TDTHVAHHLF  ATIPHYNAME  ATEAIKPILG  350
FAH12     301  GAMVTVDRDY  GVLNKVFHNI  ADTHVAHHLF  ATVPHYHAME  ATKAIKPIMG  350
ATFAD2    301  GALATVDRDY  GILNKVFHNI  TDTHVAHHLF  STMPHYNAME  ATKAIKPILG  350
BNFAD2    301  GALATVDRDY  GILNQGFHNI  TDTHEAHHLF  STMPHYHAME  ATKAIKPILG  350
GMFAD2-1  301  GALATMDRDY  GILNKVFHHI  TDTHVAHHLF  STMPHYHAME  ATNAIKPILG  350
GMFAD2-2  301  GALATMDRDY  GILNKVFHNI  TDTHVAHHLF  STMPHYHAME  ATKAIKPILG  350
ZMFAD2    301  GALATVDRDY  GILNRVFHNI  TDTHVAHHLF  STMPHYHAME  ATKAIRPILG  350
RCFAD2    301  GALATVDRDY  GILNKVFHNI  TDTQVAHHLF  ----------  ----------  350

360         370         380         390         400
LFFAH12   351  DYYHFDGTPW  YVAMYREAKE  CLYVEPDTER  GKKGVYYYNN  K-L.......  400
FAH12     351  EYYRYDGTPF  YKALWREAKE  CLFVEPDEGA  PTQGVFWYRN  KY-.......  400
ATFAD2    351  DYYQFDGTPW  YVAMYREAKE  CIYVEPDREG  DKKGVYWYNN  K-L.......  400
BNFAD2    351  EYYQFDGTPV  YKAMWREAKE  CIYVEPDRQG  EKKGVFWYNN  KL*.......  400
GMFAD2-1  351  EYYQFDDTPF  YKALWREARE  CLYVEPDEGT  SEKGVYWYRN  KY*.......  400
GMFAD2-2  351  GALATMDRDY  YKAMWREARE  CIYVEPDQST  ESKGVFWYNN  KL-.......  400
ZMFAD2    351  EYRFDETPF   VKAMWREAGE  CIYVEPE---  DRKGVFWYNK  KF*.......  400
RCFAD2    351  DYYHFDPTPV  AKATWREAGE  ----------  ----------  ----------  400
```

PRODUCTION OF HYDROXYLATED FATTY ACIDS IN GENETICALLY MODIFIED PLANTS

CROSS-REFERENCE TO RELATED APPLICATION

This application is a continuation-in-part of U.S. patent application Ser. No. 08/320,982, filed Oct. 11, 1994, which itself is a continuation-in-part of U.S. patent application Ser. No. 08/314,596, filed Sep. 26, 1994, now abandoned. The entire contents of U.S. patent application Ser. No. 08/320,982 Now U.S. Pat. No. 5,801,026 and U.S. patent application Ser. No. 08/314,596 now U.S. Pat. No. 5,688,292 are hereby incorporated by reference and relied upon.

GOVERNMENT RIGHTS

The invention described herein was made in the course of work under grant number DE-FG02-94ER20133 from the U.S. Department of Energy and grant No. MCB9305269 from the National Science Foundation. Therefore, the U.S. Government has certain rights under this invention.

TECHNICAL FIELD

The present invention concerns the identification of nucleic acid sequences and constructs, and methods related thereto, and the use of these sequences and constructs to produce genetically modified plants for the purpose of altering the fatty acid composition of plant oils, waxes and related compounds.

DEFINITIONS

The subject of this invention is a class of enzymes that introduce a hydroxyl group into several different fatty acids resulting in the production of several different kinds of hydroxylated fatty acids. In particular, these enzymes catalyze hydroxylation of oleic acid to 12-hydroxy oleic acid and icosenoic acid to 14-hydroxy icosenoic acid. Other fatty acids such as palmitoleic and erucic acids may also be substrates. Since it is not possible to refer to the enzyme by reference to a unique substrate or product, we refer to the enzyme throughout as kappa hydroxylase to indicate that the enzyme introduces the hydroxyl three carbons distal (i.e., away from the carboxyl carbon of the acyl chain) from a double bond located near the center of the acyl chain.

The following fatty acids are also the subject of this invention: ricinoleic acid, 12-hydroxyoctadec-cis-9-enoic acid ($12OH-18:1^{cis\Delta 9}$); lesquerolic acid, 14-hydroxy-cis-11-icosenoic acid ($14OH-20:1^{cis\Delta 11}$); densipolic acid, 12-hydroxyoctadec-cis-9,15-dienoic acid ($12OH-18:2^{cis\Delta 9,15}$); auricolic acid, 14-hydroxy-cis-11,17-icosadienoic acid ($14OH-20:2^{cis\Delta 11,17}$); hydroxyerucic, 16-hydroxydocos-cis-13-enoic acid ($16OH-22:1^{cis\Delta 13}$); hydroxypalmitoleic, 12-hydroxyhexadec-cis-9-enoic ($12OH-16:1^{cis\Delta 9}$); icosenoic acid ($20:1^{cis\Delta 9,11}$). It will be noted that icosenoic acid is spelled eicosenoic acid in some countries.

BACKGROUND

Extensive surveys of the fatty acid composition of seed oils from different species of higher plants have resulted in the identification of at least 33 structurally distinct mono-hydroxylated plant fatty acids, and 12 different polyhydroxylated fatty acids that are accumulated by one or more plant species (reviewed by van de Loo et al. 1993). Ricinoleic acid, the principal constituent of the seed oil from the castor plant Ricinus communis (L.), is of commercial importance. We have previously described the cloning of a gene from this species that encodes a fatty acid hydroxylase, and the use of this gene to produce ricinoleic acid in transgenic plants of other species (see U.S. patent application Ser. No. 08/320,982, filed Oct. 11, 1994). The scientific evidence supporting the claims in that patent application were subsequently published (van de Loo et al., 1995). The use of the castor hydroxylase gene to also produce other hydroxylated fatty acids such as lesquerolic acid, densipolic acid, hydroxypalmitoleic, hydroxyerucic and auricolic acid in transgenic plants is the subject of this invention. In addition, the identification of a gene encoding a homologous hydroxylase from Lesquerella fendleri, and the use of this gene to produce these hydroxylated fatty acids in transgenic plants is the subject of this invention.

Castor is a minor oilseed crop. Approximately 50% of the seed weight is oil (triacylglycerol) in which 85–90% of total fatty acids are the hydroxylated fatty acid, ricinoleic acid. Oil pressed or extracted from castor seeds has many industrial uses based upon the properties endowed by the hydroxylated fatty acid. The most important uses are production of paints and varnishes, nylon-type synthetic polymers, resins, lubricants, and cosmetics (Atsmon 1989). In addition to oil, the castor seed contains the extremely toxic protein ricin, allergenic proteins, and the alkaloid ricinine. These constituents preclude the use of the untreated seed meal (following oil extraction) as a livestock feed, normally an important economic aspect of oilseed utilization. Furthermore, with the variable nature of castor plants and a lack of investment in breeding, castor has few favorable agronomic characteristics. For a combination of these reasons, castor is no longer grown in the United States and the development of an alternative domestic source of hydroxylated fatty acids would be attractive. The production of ricinoleic acid, the important constituent of castor oil, in an established oilseed crop through genetic engineering would be a particularly effective means of creating a domestic source.

Because there is no practical source of lesquerolic, densipolic and auricolic acids from plants that are adapted to modern agricultural practices, there is currently no large-scale use of these fatty acids by industry. However, the fatty acids would have uses similar to those of ricinoleic acid if they could be produced in large quantities at comparable cost to other plant-derived fatty acids (Smith 1985). Plant species, such as certain species in the genus Lesquerella, that accumulate a high proportion of these fatty acids, have not been domesticated and are not currently considered a practical source of fatty acids (Hirsinger, 1989). This invention represents a useful step toward the eventual production of these and other hydroxylated fatty acids in transgenic plants of agricultural importance.

The taxonomic relationships between plants having similar or identical kinds of unusual fatty acids have been examined (van de Loo et al., 1993). In some cases, particular fatty acids occur mostly or solely in related taxa. In other cases there does not appear to be a direct link between taxonomic relationships and the occurrence of unusual fatty acids. In this respect, ricinoleic acid has now been identified in 12 genera from 10 families (reviewed in van de Loo et al., 1993). Thus, it appears that the ability to synthesize hydroxylated fatty acids has evolved several times independently during the radiation of the angiosperms. This suggested to us that the enzymes which introduce hydroxyl groups into fatty acids arose by minor modifications of a related enzyme. Indeed, as shown herein, the sequence similarity between Δ12 fatty acid desaturases and the kappa hydroxylase from castor is so high that it is not possible to unambiguously determine whether a particular enzyme is a desaturase or a hydroxylase on the basis of evidence in the scientific literature. Similarly, a patent application (PCT/US93/09987) that purports to teach the isolation and use of Δ12 fatty acid desaturases does not teach how to distinguish a hydroxylase from a desaturase. In view of the importance of being able to distinguish between these activities for the purpose of genetic engineering of plant oils, the utility of that application is limited to the several instances where direct experimental evidence (e.g., altered fatty acid composition in transgenic plants) was presented to support the assignment of function. A method for distinguishing between fatty acid desaturases and fatty acid hydroxylases on the basis of amino acid sequence of the enzyme is also a subject of this invention.

A feature of hydroxylated or other unusual fatty acids is that they are generally confined to seed triacylglycerols, being largely excluded from the polar lipids by unknown mechanisms (Battey and Ohlrogge 1989; Prasad et al., 1987). This is particularly intriguing since diacylglycerol is a precursor of both triacylglycerol and polar lipid. With castor microsomes, there is some evidence that the pool of ricinoleoyl-containing polar lipid is minimized by a preference of diacylglycerol acyltransferase for ricinoleate-containing diacylglycerols (Bafor et al. 1991). Analyses of vegetative tissues have generated few reports of unusual fatty acids, other than those occurring in the cuticle. The cuticle contains various hydroxylated fatty acids which are interesterified to produce a high molecular weight polyester which serves a structural role. A small number of other exceptions exist in which unusual fatty acids are found in tissues other than the seed.

The biosynthesis of ricinoleic acid from oleic acid in the developing endosperm of castor (*Ricinus communis*) has been studied by a variety of methods. Morris (1967) established in double-labeling studies that hydroxylation occurs directly by hydroxyl substitution rather than via an unsaturated-, keto- or epoxy-intermediate. Hydroxylation using oleoyl-CoA as precursor can be demonstrated in crude preparations or microsomes, but activity in microsomes is unstable and variable, and isolation of the microsomes involved a considerable, or sometimes complete loss of activity (Galliard and Stumpf, 1966; Moreau and Stumpf, 1981). Oleic acid can replace oleoyl-CoA as a precursor, but only in the presence of CoA, $Mg^{2+}$ and ATP (Galliard and Stumpf, 1966) indicating that activation to the acyl-CoA is necessary. However, no radioactivity could be detected in ricinoleoyl-CoA (Moreau and Stumpf, 1981). These and more recent observations (Bafor et al., 1991) have been interpreted as evidence that the substrate for the castor oleate hydroxylase is oleic acid esterified to phosphatidylcholine or another phospholipid.

The hydroxylase is sensitive to cyanide and azide, and dialysis against metal chelators reduces activity, which could be restored by addition of $FeSO_4$, suggesting iron involvement in enzyme activity (Galliard and Stumpf, 1966). Ricinoleic acid synthesis requires molecular oxygen (Galliard and Stumpf, 1966; Moreau and Stumpf 1981) and requires NAD(P)H to reduce cytochrome b5 which is thought to be the intermediate electron donor for the hydroxylase reaction (Smith et al., 1992). Carbon monoxide does not inhibit hydroxylation, indicating that a cytochrome P450 is not involved (Galliard and Stumpf, 1966; Moreau and Stumpf 1981). Data from a study of the substrate specificity of the hydroxylase show that all substrate parameters (i.e., chain length and double bond position with respect to both ends) are important; deviations in these parameters caused reduced activity relative to oleic acid (Howling et al., 1972). The position at which the hydroxyl was introduced, however, was determined by the position of the double bond, always being three carbons distal. Thus, the castor acyl hydroxylase enzyme can produce a family of different hydroxylated fatty acids depending on the availability of substrates. Thus, as a matter of convenience, we refer to the enzyme throughout as a kappa hydroxylase (rather than an oleate hydroxylase) to indicate the broad substrate specificity.

The castor kappa hydroxylase has many superficial similarities to the microsomal fatty acyl desaturases (Browse and Somerville, 1991). In particular, plants have a microsomal oleate desaturase active at the Δ12 position. The substrate of this enzyme (Schmidt et al., 1993) and of the hydroxylase (Bafor et al., 1991) appears to be a fatty acid esterified to the sn-2 position of phosphatidylcholine. When oleate is the substrate, the modification occurs at the same position (Δ12) in the carbon chain, and requires the same cofactors, namely electrons from NADH via cytochrome $b_5$ and molecular oxygen. Neither enzyme is inhibited by carbon monoxide (Moreau and Stumpf, 1981), the characteristic inhibitor of cytochrome P450 enzymes.

There do not appear to have been any published biochemical studies of the properties of the hydroxylase enzyme(s) in Lesquerella.

Conceptual Basis of the Invention

In U.S. patent application Ser. No. 08/320,982, we described the use of a cDNA clone from castor for the production of ricinoleic acid in transgenic plants. As noted above, biochemical studies by others had suggested that the castor hydroxylase may not have strict specificity for oleic acid but would also catalyze hydroxylation of other fatty acids such as icosenoic acid ($20:1^{cis\Delta 11}$) (Howling et al., 1972). Based on these studies, our previous application No. 08/320,982 noted in Example 2 that the expression of the castor hydroxylase in transgenic plants of species such as *Brassica napus* and *Arabidopsis thaliana* that accumulate fatty acids such as icosenoic acid ($20:1^{cis\Delta 11}$) and erucic acid (13-docosenoic acid; $22:^{cis\Delta 13}$) would be expected to accumulate some of the hydroxylated derivatives of these fatty acids due to the activity of the hydroxylase on these fatty acids. We have now obtained additional direct evidence for such a claim based on the production of ricinoleic, lesquerolic, densipolic and auricolic fatty acids in transgenic Arabidopsis plants and have included such evidence herein as Example 1.

In example three of the previous application, we taught the various methods by which the castor hydroxylase clone and sequences derived thereof could be used to identify other hydroxylase clones from plant species such as *Lesquerella fendleri* that are known to accumulate hydroxylated fatty acids in seed oils. In this continuation we have provided an example of the use of that aspect of the invention for the isolation of a novel hydroxylase gene from *Lesquerella fendleri*.

In view of the high degree of sequence similarity between Δ12 fatty acid desaturases and the castor hydroxylase (van de Loo et al., 1995), the validity of claims for the use of desaturase or hydroxylase genes or sequences derived therefrom for the identification of genes of identical function from other species must be viewed with skepticism. In this application, we teach a method by which hydroxylase genes can be distinguished from desaturases and describe methods by which Δ12 desaturases can be converted to hydroxylases by the modification of the gene encoding the desaturases. A mechanistic basis for the similar reaction mechanisms of desaturases and hydroxylases was presented in the earlier patent application (No. 08/320,982). Briefly, the available evidence suggests that fatty acid desaturases have a similar reaction mechanism to the bacterial enzyme methane monooxygenase which catalyses a reaction involving oxygen-atom transfer ($CH_4 \rightarrow CH_3OH$) (van de Loo et al., 1993). The cofactor in the hydroxylase component of methane monooxygenase is termed a μ-oxo bridged diiron cluster (FeOFe). The two iron atoms of the FeOFe cluster are liganded by protein-derived nitrogen or oxygen atoms, and are tightly redox-coupled by the covalently-bridging oxygen atom. The FeOFe cluster accepts two electrons, reducing it to the diferrous state, before oxygen binding. Upon oxygen binding, it is likely that heterolytic cleavage also occurs, leading to a high valent oxoiron reactive species that is stabilized by resonance rearrangements possible within the tightly coupled FeOFe cluster. The stabilized high-valent oxoiron state of methane monooxygenase is capable of proton extraction from methane, followed by oxygen transfer, giving methanol. The FeOFe cofactor has been shown to be directly relevant to plant fatty acid modifications by the demonstration that castor stearoyl-ACP desaturase contains this type of cofactor (Fox et al., 1993).

On the basis of the foregoing considerations, we hypothesized that the castor oleate hydroxylase is a structurally modified fatty acyl desaturase, based upon three arguments. The first argument involves the taxonomic distribution of plants containing ricinoleic acid. Ricinoleic acid has been found in 12 genera of 10 families of higher plants (reviewed in van de Loo et al., 1993). Thus, plants in which ricinoleic acid occurs are found throughout the plant kingdom, yet close relatives of these plants do not contain the unusual fatty acid. This pattern suggests that the ability to synthesize ricinoleic acid has arisen (and been lost) several times independently, and is therefore a quite recent divergence. In other words, the ability to synthesize ricinoleic acid has evolved rapidly, suggesting that a relatively minor genetic change in the structure of the ancestral enzyme was necessary to accomplish it.

The second argument is that many biochemical properties of castor kappa hydroxylase are similar to those of the microsomal desaturases, as discussed above (e.g., both preferentially act on fatty acids esterified to the sn-2 position of phosphatidylcholine, both use cytochrome b5 as an intermediate electron donor, both are inhibited by cyanide, both require molecular oxygen as a substrate, both are thought to be located in the endoplasmic reticulum).

The third argument stems from the discussion of oxygenase cofactors above, in which it is suggested that the plant membrane bound fatty acid desaturases may have a μ-oxo bridged diiron cluster-type cofactor, and that such cofactors are capable of catalyzing both fatty acid desaturations and hydroxylations, depending upon the electronic and structural properties of the protein active site.

Taking these three arguments together, it was hypothesized that kappa hydroxylase of castor endosperm is homologous to the microsomal oleate Δ12 desaturase found in all plants. The evidence supporting this hypothesis was disclosed in the previous patent application (No. 08/320, 982). A number of genes encoding microsomal Δ12 desaturases from various species have recently been cloned (Okuley et al., 1994) and substantial information about the structure of these enzymes is now known. Hence, in the following invention we teach how to use structural information about fatty acyl desaturases to isolate kappa hydroxylase genes of this invention. This example teaches the method by which any carbon-monoxide insensitive plant fatty acyl hydroxylase gene can be identified by one skilled in the art.

BRIEF DESCRIPTION OF THE DRAWINGS

FIG. 1B, O-TMS-methyl densipoleate; FIG. 1C, O-TMS-methyl-lesqueroleate; and FIG. 1D, O-TMS-methylauricoleate).

FIG. 2 shows the fragmentation pattern of trimethylsilylated methyl esters of hydroxy fatty acids.

FIG. 4A shows the mass spectrum of peak 10 from FIG. 3B. FIG. 4B shows the mass spectrum of peak 11 from FIG. 3B. FIG. 4C shows the mass spectrum of peak 12 from FIG. 3B. FIG. 4D shows the mass spectrum of peak 13 from FIG. 3B.

FIG. 5 shows the nucleotide sequence of pLesq2 (SEQ ID NO:1).

FIG. 6 shows the nucleotide sequence of pLesq3 (SEQ ID NO:2).

FIGS. 8A–B show the nucleotide sequence of genomic clone encoding pLesq-HYD (SEQ ID NO:3), and the deduced amino acid sequence of hydroxylase enzyme encoded by the gene (SEQ ID NO:4).

FIGS. 9A–B show multiple sequence alignment of deduced amino acid sequences for kappa hydroxylases and microsomal Δ12 desaturases. Abbreviations are: Rcfah12, fah12 hydroxylase gene from R. communis (van de Loo et al., 1995); Lffah12, kappa hydroxylase gene from L. fendleri; Atfad2, fad2 desaturase from Arabidopsis thaliana (Okuley et al., 1994); Gmfad2-1, fad2 desaturase from Glycine max (GenBank accession number L43920); Gmfad2-2, fad2 desaturase from Glycine max (Genbank accession number L43921); Zmfad2, fad2 desaturase from Zea mays (PCT/US93/09987); Rcfad2, fragment of fad2 desaturase from R. communis (PCT/US93/09987); Bnfad2, fad2 desaturase from Brassica napus (PCT/US93/09987); LFFAH12.AMI, SEQ ID NO:4; FAH12.AMI, SEQ ID NO:5; ATFAD2.AMI, SEQ ID NO:6; BNFAD2.AMI, SEQ ID NO:7; GMFAD2-1.AMI, SEQ ID NO:8; GMFAD2-2.AMI, SEQ ID NO:9; ZMFAD2.AMI, SEQ ID NO:10; and RCFAD2.AMI, SEQ ID NO:11.

SUMMARY OF THE INVENTION

Figure 1A:
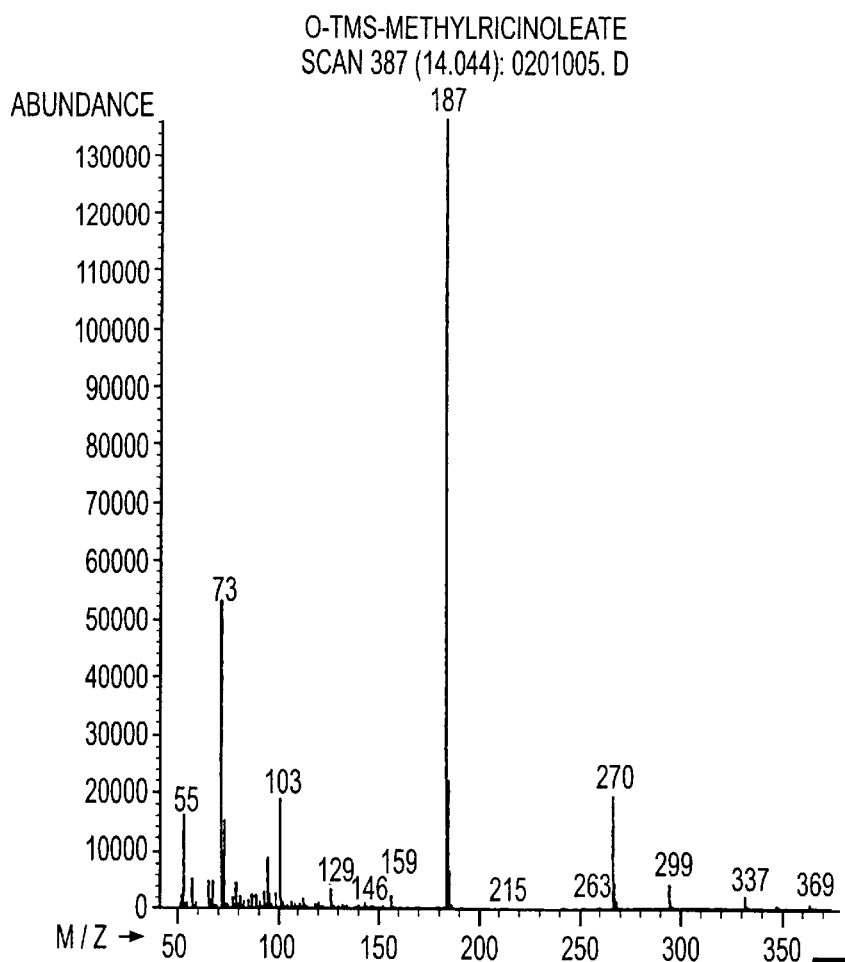
FIGS. 1A–D show the mass spectra of hydroxy fatty acids standards (FIG. 1A, O-TMS-methylricinoleate.
Figure 1B:
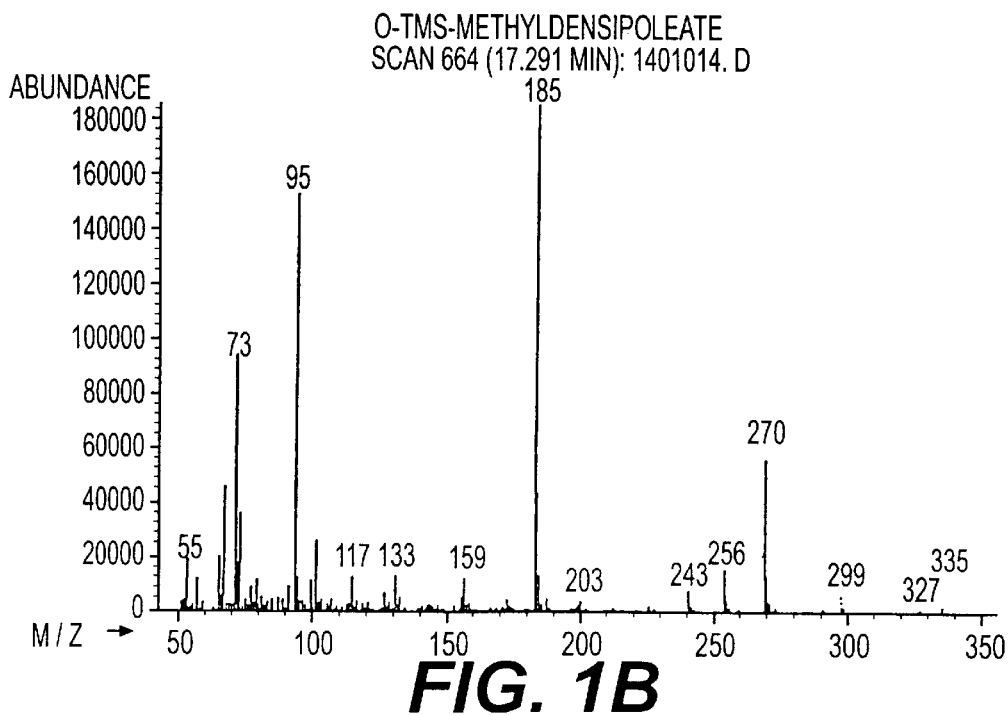
Figure 1C:
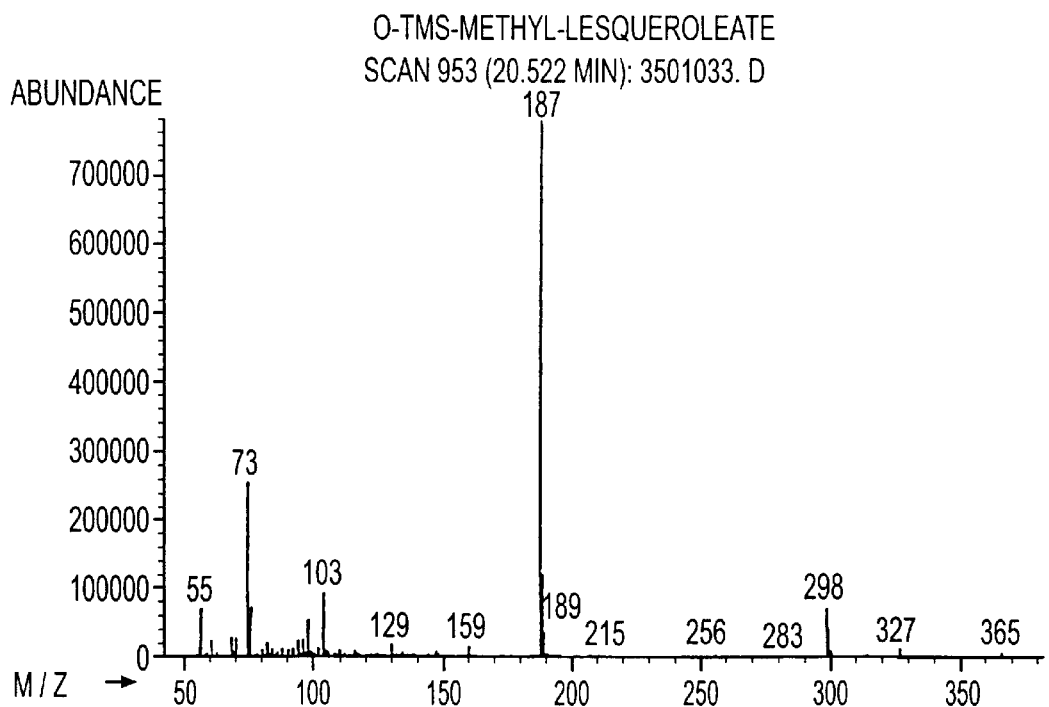
Figure 1D:
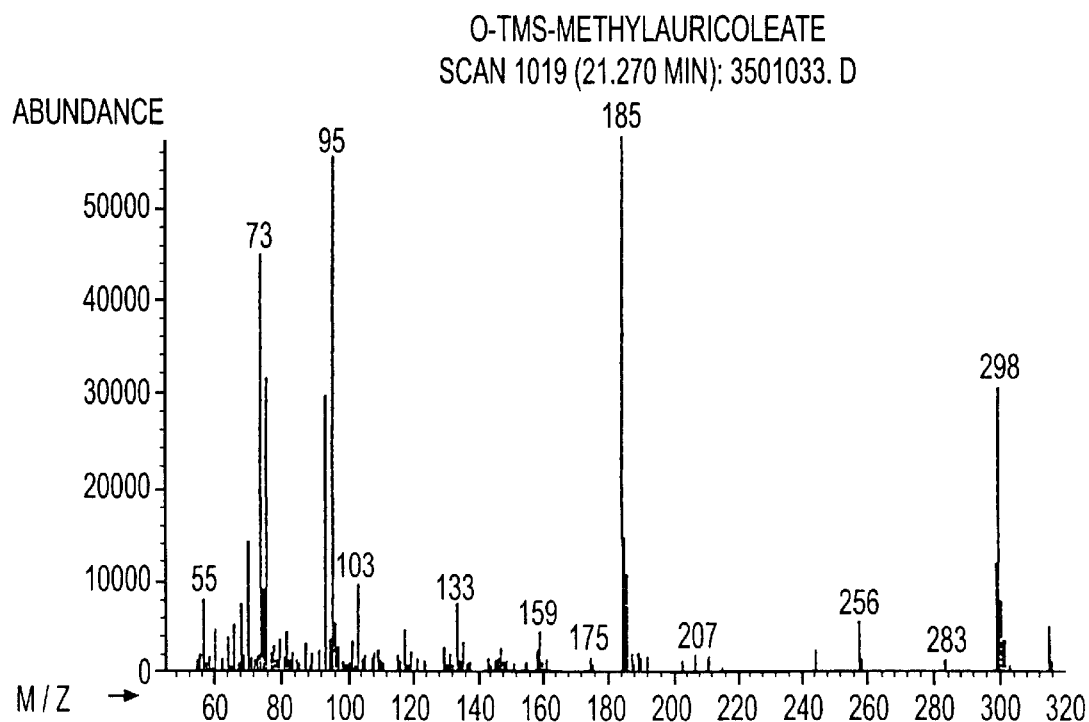

This invention relates to plant fatty acyl hydroxylases. Methods to use conserved amino acid or nucleotide sequences to obtain plant fatty acyl hydroxylases are described. Also described is the use of cDNA clones encoding a plant hydroxylase to produce a family of hydroxylated fatty acids in transgenic plants.

In a first embodiment, this invention is directed to recombinant DNA constructs which can provide for the transcription or transcription and translation (expression) of the plant kappa hydroxylase sequence. In particular, constructs which are capable of transcription or transcription and translation in plant host cells are preferred. Such constructs may contain a variety of regulatory regions including transcriptional initiation regions obtained from genes preferentially expressed in plant seed tissue. In a second aspect, this invention relates to the presence of such constructs in host cells, especially plant host cells which have an expressed plant kappa hydroxylase therein.

In yet another aspect, this invention relates to a method for producing a plant kappa hydroxylase in a host cell or progeny thereof via the expression of a construct in the cell. Cells containing a plant kappa hydroxylase as a result of the production of the plant kappa hydroxylase encoding sequence are also contemplated herein.

In another embodiment, this invention relates to methods of using a DNA sequence encoding a plant kappa hydroxylase for the modification of the proportion of hydroxylated fatty acids produced within a cell, especially plant cells. Plant cells having such a modified hydroxylated fatty acid composition are also contemplated herein.

In a further aspect of this invention, plant kappa hydroxylase proteins and sequences which are related thereto, including amino acid and nucleic acid sequences, are contemplated. Plant kappa hydroxylase exemplified herein includes a *Lesquerella fendleri* fatty acid hydroxylase. This exemplified fatty acid hydroxylase may be used to obtain other plant fatty acid hydroxylases of this invention.

In a further aspect of this invention, a nucleic acid sequence which directs the seed specific expression of an associated polypeptide coding sequence is described. The use of this nucleic acid sequence or fragments derived thereof, to obtain seed-specific expression in higher plants of any coding sequence is contemplated herein.

DETAILED DESCRIPTION OF THE INVENTION

A genetically transformed plant of the present invention which accumulates hydroxylated fatty acids can be obtained by expressing the double-stranded DNA molecules described in this application.

A plant fatty acid hydroxylase of this invention includes any sequence of amino acids, such as a protein, polypeptide or peptide fragment, or nucleic acid sequences encoding such polypeptides, obtainable from a plant source which demonstrates the ability to catalyze the production of ricinoleic, lesquerolic, hydroxyerucic (16-hydroxydocos-cis-13-enoic acid) or hydroxypalmitoleic (12-hydroxyhexadec-cis-9-enoic) from CoA, ACP or lipid-linked monoenoic fatty acid substrates under plant enzyme reactive conditions. By "enzyme reactive conditions" is meant that any necessary conditions are available in an environment (i.e., such factors as temperature, pH, lack of inhibiting substances) which will permit the enzyme to function.

Preferential activity of a plant fatty acid hydroxylase toward a particular fatty acyl substrate is determined upon comparison of hydroxylated fatty acid product amounts obtained per different fatty acyl substrates. For example, by "oleate preferring" is meant that the hydroxylase activity of the enzyme preparation demonstrates a preference for oleate-containing substrates over other substrates. Although the precise substrate of the castor fatty acid hydroxylase is not known, it is thought to be a monounsaturated fatty acid moiety which is esterified to a phospholipid such as phosphatidylcholine. However, it is also possible that monounsaturated fatty acids esterified to phosphatidylethanolamine, phosphatidic acid or a neutral lipid such as diacylglycerol or a Coenzyme-A thioester may also be substrates. As noted above, significant activity has been observed in radioactive labelling studies using fatty acyl substrates other than oleate (Howling et al., 1972) indicating that the substrate specificity is for a family of related fatty acyl compounds. Because the castor hydroxylase introduces hydroxy groups three carbons from a double bond, proximal to the methyl carbon of the fatty acid we term the enzyme a kappa hydroxylase for convenience. Of particular interest, we envision that the castor kappa hydroxylase may be used for production of 12-hydroxy-9-octadecenoic acid (ricinoleate), 12-hydroxy-9-hexadecenoic acid, 14-hydroxy-11-eicosenoic acid, 16-hydroxy-13-docosenic acid, 9-hydroxy-6-octadecenoic acid by expression in plants species which produce the non-hydroxylated precursors. We also envision production of additionally modified fatty acids such as 12-hydroxy-9,15-octadecadienoic acid that result from desaturation of hydroxylated fatty acids (e.g., 12-hydroxy-9-octadecenoic acid in this example).

We also envision that future advances in the genetic engineering of plants will lead to production of substrate fatty acids, such as icosenoic acid esters, and palmitoleic acid esters in plants that do not normally accumulate such fatty acids. We envision that the invention described herein may be used in conjunction with such future improvements to produce hydroxylated fatty acids of this invention in any plant species that is amenable to directed genetic modification. Thus, the applicability of this invention is not limited in our conception only to those species that currently accumulate suitable substrates.

As noted above, a plant kappa hydroxylase of this invention will display activity towards various fatty acyl substrates. During biosynthesis of lipids in a plant cell, fatty acids are typically covalently bound to acyl carrier protein (ACP), coenzyme A (CoA) or various cellular lipids. Plant kappa hydroxylases which display preferential activity toward lipid-linked acyl substrate are especially preferred because they are likely to be closely associated with normal pathway of storage lipid synthesis in immature embryos. However, activity toward acyl-CoA substrates or other synthetic substrates, for example, is also contemplated herein.

Other plant kappa hydroxylases are obtainable from the specific exemplified sequences provided herein. Furthermore, it will be apparent that one can obtain natural and synthetic plant kappa hydroxylases including modified amino acid sequences and starting materials for synthetic-protein modeling from the exemplified plant kappa hydroxylase and from plant kappa hydroxylases which are obtained through the use of such exemplified sequences. Modified amino acid sequences include sequences which have been mutated, truncated, increased and the like, whether such sequences were partially or wholly synthesized. Sequences which are actually purified from plant preparations or are identical or encode identical proteins thereto, regardless of the method used to obtain the protein or sequence, are equally considered naturally derived.

Thus, one skilled in the art will readily recognize that antibody preparations, nucleic acid probes (DNA and RNA)

and the like may be prepared and used to screen and recover "homologous" or "related" kappa hydroxylases from a variety of plant sources. Typically, nucleic acid probes are labeled to allow detection, preferably with radioactivity although enzymes or other methods may also be used. For immunological screening methods, antibody preparations either monoclonal or polyclonal are utilized. Polyclonal antibodies, although less specific, typically are more useful in gene isolation. For detection, the antibody is labeled using radioactivity or any one of a variety of second antibody/enzyme conjugate systems that are commercially available.

Homologous sequences are found when there is an identity of sequence and may be determined upon comparison of sequence information, nucleic acid or amino acid, or through hybridization reactions between a known kappa hydroxylase and a candidate source. Conservative changes, such as Glu/Asp, Val/Ile, Ser/Thr, Arg/Lys and Gln/Asn may also be considered in determining sequence homology. Typically, a lengthy nucleic acid sequence may show as little as 50–60% sequence identity, and more preferably at least about 70% sequence identity, between the target sequence and the given plant kappa hydroxylase of interest excluding any deletions which may be present, and still be considered related. Amino acid sequences are considered homologous by as little as 25% sequence identity between the two complete mature proteins. (See generally, Doolittle, R. F., OF URFS and ORFS, University Science Books, California, 1986.)

A genomic or other appropriate library prepared from the candidate plant source of interest may be probed with conserved sequences from the plant kappa hydroxylase to identify homologously related sequences. Use of an entire cDNA or other sequence may be employed if shorter probe sequences are not identified. Positive clones are then analyzed by restriction enzyme digestion and/or sequencing. When a genomic library is used, one or more sequences may be identified providing both the coding region, as well as the transcriptional regulatory elements of the kappa hydroxylase gene from such plant source. Probes can also be considerably shorter than the entire sequence. Oligonucleotides may be used, for example, but should be at least about 10, preferably at least about 15, more preferably at least 20 nucleotides in length. When shorter length regions are used for comparison, a higher degree of sequence identity is required than for longer sequences. Shorter probes are often particularly useful for polymerase chain reactions (PCR), especially when highly conserved sequences can be identified (See Gould, et al., 1989 for examples of the use of PCR to isolate homologous genes from taxonomically diverse species).

When longer nucleic acid fragments are employed (>100 bp) as probes, especially when using complete or large cDNA sequences, one would screen with low stringencies (for example, 40–50° C. below the melting temperature of the probe) in order to obtain signal from the target sample with 20–50% deviation, i.e., homologous sequences. (Beltz, et al. 1983).

In a preferred embodiment, a plant kappa hydroxylase of this invention will have at least 60% overall amino acid sequence similarity with the exemplified plant kappa hydroxylase. In particular, kappa hydroxylases which are obtainable from an amino acid or nucleic acid sequence of a castor or lesquerella kappa hydroxylase are especially preferred. The plant kappa hydroxylases may have preferential activity toward longer or shorter chain fatty acyl substrates. Plant fatty acyl hydroxylases having oleate-12-hydroxylase activity and eicosenoate-14-hydroxylase activity are both considered homologously related proteins because of in vitro evidence (Howling et al., 1972), and evidence disclosed herein, that the castor kappa hydroxylase will act on both substrates. Hydroxylated fatty acids may be subject to further enzymatic modification by other enzymes which are normally present or are introduced by genetic engineering methods. For example, 14-hydroxy-11,17-eicosadienoic acid, which is present in some Lesquerella species (Smith 1985), is thought to be produced by desaturation of 14-hydroxy-11-eicosenoic acid.

Again, not only can gene clones and materials derived thereof be used to identify homologous plant fatty acyl hydroxylases, but the resulting sequences obtained therefrom may also provide a further method to obtain plant fatty acyl hydroxylases from other plant sources. In particular, PCR may be a useful technique to obtain related plant fatty acyl hydroxylases from sequence data provided herein. One skilled in the art will be able to design oligonucleotide probes based upon sequence comparisons or regions of typically highly conserved sequence. Of special interest are polymerase chain reaction primers based on the conserved regions of amino acid sequence between the castor kappa hydroxylase and the *L. fendleri* hydroxylase (SEQ ID NO:4). Details relating to the design and methods for a PCR reaction using these probes are described more fully in the examples.

It should also be noted that the fatty acyl hydroxylases of a variety of sources can be used to investigate fatty acid hydroxylation events in a wide variety of plant and in vivo applications. Because all plants synthesize fatty acids via a common metabolic pathway, the study and/or application of one plant fatty acid hydroxylase to a heterologous plant host may be readily achieved in a variety of species.

Once the nucleic acid sequence is obtained, the transcription, or transcription and translation (expression), of the plant fatty acyl hydroxylases in a host cell is desired to produce a ready source of the enzyme and/or modify the composition of fatty acids found therein in the form of free fatty acids, esters (particularly esterified to glycerolipids or as components of wax esters), estolides, or ethers. Other useful applications may be found when the host cell is a plant host cell, in vitro and in vivo.

For example, by increasing the amount of an kappa hydroxylase available to the plant, an increased percentage of ricinoleate or lesqueroleate (14-hydroxy-11-eicosenoic acid) may be provided.

Kappa Hydroxylase

By this invention, a mechanism for the biosynthesis of ricinoleic acid in plants is demonstrated. Namely, that a specific plant kappa hydroxylase having preferential activity toward fatty acyl substrates is involved in the accumulation of hydroxylated fatty acids in at least some plant species. The use of the terms ricinoleate or ricinoleic acid (or lesqueroleate or lesquerolic acid, densipoleate etc.) is intended to include the free acids, the ACP and CoA esters, the salts of these acids, the glycerolipid esters (particularly the triacylglycerol esters), the wax esters, the estolides and the ether derivatives of these acids.

The determination that plant fatty acyl hydroxylases are active in the in vivo production of hydroxylated fatty acids suggests several possibilities for plant enzyme sources. And in fact, hydroxylated fatty acids are found in some natural plant species in abundance. For example, three hydroxy fatty acids related to ricinoleate occur in major amounts in seed oils from various Lesquerella species. Of particular interest, lesquerolic acid is a 20 carbon homolog of ricinoleate with two additional carbons at the carboxyl end of the chain (Smith 1985). Other natural plant sources of hydroxylated fatty acids include but are not limited to seeds of the Linum genus, seeds of Wrightia species, Lycopodium species, Strophanthus species, Convolvulaces species, Calendula species and many others (van de Loo et al., 1993).

Plants having significant presence of ricinoleate or lesqueroleate or desaturated other or modified derivatives of these fatty acids are preferred candidates to obtain naturally-derived kappa hydroxylases. For example, *Lesquerella densipila* contains a diunsaturated 18 carbon fatty acid with a hydroxyl group (van de Loo et al., 1993) that is thought to be produced by an enzyme that is closely related to the castor kappa hydroxylase, according to the theory on which this invention is based. In addition, a comparison between kappa hydroxylases and between plant fatty acyl hydroxylases which introduce hydroxyl groups at positions other than the 12-carbon of oleate or the 14-carbon of lesqueroleate or on substrates other than oleic acid and icosenoic acid may yield insights for protein modeling or other modifications to create synthetic hydroxylases as discussed above. For example, on the basis of information gained from structural comparisons of the Δ12 desaturases and the kappa hydroxylase, we envision making genetic modifications in the structural genes for Δ12 desaturases that convert these desaturases to kappa-hydroxylases. We also envision making changes in Δ15 hydroxylases that convert these to hydroxylases with comparable substrate specificity to the desaturases (e.g., conversion of $18:2^{\Delta 9,12}$ to $15OH-18:2^{\Delta 9,12}$. Since the difference between a hydroxylase and a desaturases concerns the disposition of one proton, we envision that by systematically changing the charged groups in the region of the enzyme near the active site, we can effect this change.

Especially of interest are fatty acyl hydroxylases which demonstrate activity toward fatty acyl substrates other than oleate, or which introduce the hydroxyl group at a location other than the C12 carbon. As described above, other plant sources may also provide sources for these enzymes through the use of protein purification, nucleic acid probes, antibody preparations, protein modeling, or sequence comparisons, for example, and of special interest are the respective amino acid and nucleic acid sequences corresponding to such plant fatty acyl hydroxylases. Also as previously described, once a nucleic acid sequence is obtained for the given plant hydroxylase, further plant sequences may be compared and/or probed to obtain homologously related DNA sequences thereto and so on.

Genetic Engineering Applications

As is well known in the art, once a cDNA clone encoding a plant kappa hydroxylase is obtained, it may be used to obtain its corresponding genomic nucleic acid sequences thereto.

The nucleic acid sequences which encode plant kappa hydroxylases may be used in various constructs, for example, as probes to obtain further sequences from the same or other species. Alternatively, these sequences may be used in conjunction with appropriate regulatory sequences to increase levels of the respective hydroxylase of interest in a host cell for the production of hydroxylated fatty acids or study of the enzyme in vitro or in vivo or to decrease or increase levels of the respective hydroxylase of interest for some applications when the host cell is a plant entity, including plant cells, plant parts (including but not limited to seeds, cuttings or tissues) and plants.

A nucleic acid sequence encoding a plant kappa hydroxylase of this invention may include genomic, cDNA or mRNA sequence. By "encoding" is meant that the sequence corresponds to a particular amino acid sequence either in a sense or anti-sense orientation. By "recombinant" is meant that the sequence contains a genetically engineered modification through manipulation via mutagenesis, restriction enzymes, and the like. A cDNA sequence may or may not encode pre-processing sequences, such as transit or signal peptide sequences. Transit or signal peptide sequences facilitate the delivery of the protein to a given organelle and are frequently cleaved from the polypeptide upon entry into the organelle, releasing the "mature" sequence. The use of the precursor DNA sequence is preferred in plant cell expression cassettes.

Furthermore, as discussed above the complete genomic sequence of the plant kappa hydroxylase may be obtained by the screening of a genomic library with a probe, such as a cDNA probe, and isolating those sequences which regulate expression in seed tissue. In this manner, the transcription and translation initiation regions, introns, and/or transcript termination regions of the plant kappa hydroxylase may be obtained for use in a variety of DNA constructs, with or without the kappa hydroxylase structural gene. Thus, nucleic acid sequences corresponding to the plant kappa hydroxylase of this invention may also provide signal sequences useful to direct transport into an organelle 5' upstream non-coding regulatory regions (promoters) having useful tissue and timing profiles, 3' downstream non-coding regulatory region useful as transcriptional and translational regulatory regions and may lend insight into other features of the gene.

Once the desired plant kappa hydroxylase nucleic acid sequence is obtained, it may be manipulated in a variety of ways. Where the sequence involves non-coding flanking regions, the flanking regions may be subjected to resection, mutagenesis, etc. Thus, transitions, transversions, deletions, and insertions may be performed on the naturally occurring sequence. In addition, all or part of the sequence may be synthesized. In the structural gene, one or more codons may be modified to provide for a modified amino acid sequence, or one or more codon mutations may be introduced to provide for a convenient restriction site or other purpose involved with construction or expression. The structural gene may be further modified by employing synthetic adapters, linkers to introduce one or more convenient restriction sites, or the like.

The nucleic acid or amino acid sequences encoding a plant kappa hydroxylase of this invention may be combined with other non-native, or "heterologous", sequences in a variety of ways. By "heterologous" sequences is meant any sequence which is not naturally found joined to the plant kappa hydroxylase, including, for example, combination of nucleic acid sequences from the same plant which are not naturally found joined together.

The DNA sequence encoding a plant kappa hydroxylase of this invention may be employed in conjunction with all or part of the gene sequences normally associated with the kappa hydroxylase. In its component parts, a DNA sequence encoding kappa hydroxylase is combined in a DNA construct having, in the 5' to 3' direction of transcription, a transcription initiation control region capable of promoting transcription and translation in a host cell, the DNA sequence encoding plant kappa hydroxylase and a transcription and translation termination region.

Potential host cells include both prokaryotic and eukaryotic cells. A host cell may be unicellular or found in a multicellular differentiated or undifferentiated organism depending upon the intended use. Cells of this invention may be distinguished by having a plant kappa hydroxylase foreign to the wild-type cell present therein, for example, by having a recombinant nucleic acid construct encoding a plant kappa hydroxylase therein.

Depending upon the host, the regulatory regions will vary, including regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as E. coli, B. subtilis, Saccharomyces cerevisiae, including genes such as beta-galactosidase, T7 polymerase, tryptophan E and the like.

For the most part, the constructs will involve regulatory regions functional in plants which provide for modified production of plant kappa hydroxylase with resulting modification of the fatty acid composition. The open reading frame, coding for the plant kappa hydroxylase or functional fragment thereof will be joined at its 5' end to a transcription initiation regulatory region such as the wild-type sequence naturally found 5' upstream to the kappa hydroxylase structural gene. Numerous other transcription initiation regions are available which provide for a wide variety of constitutive or regulatable, e.g., inducible, transcription of the structural gene functions. Among transcriptional initiation regions used for plants are such regions associated with the structural genes such as for nopaline and mannopine synthases, or with napin, soybean β-conglycinin, oleosin, 12S storage protein, the cauliflower mosaic virus 35S promoters and the like. The transcription/translation initiation regions corresponding to such structural genes are found immediately 5' upstream to the respective start codons. In embodiments wherein the expression of the kappa hydroxylase protein is desired in a plant host, the use of all or part of the complete plant kappa hydroxylase gene is desired; namely all or part of the 5' upstream non-coding regions (promoter) together with the structural gene sequence and 3' downstream non-coding regions may be employed. If a different promoter is desired, such as a promoter native to the plant host of interest or a modified promoter, i.e., having transcription initiation regions derived from one gene source and translation initiation regions derived from a different gene source, including the sequence encoding the plant kappa hydroxylase of interest, or enhanced promoters, such as double 35S CaMV promoters, the sequences may be joined together using standard techniques.

For such applications when 5' upstream non-coding regions are obtained from other genes regulated during seed maturation, those preferentially expressed in plant embryo tissue, such as transcription initiation control regions from the B. napus napin gene, or the Arabidopsis 12S storage protein, or soybean β-conglycinin (Bray et al., 1987), or the L. fendleri kappa hydroxylase promoter described herein are desired. Transcription initiation regions which are preferentially expressed in seed tissue, i.e., which are undetectable in other plant parts, are considered desirable for fatty acid modifications in order to minimize any disruptive or adverse effects of the gene product.

Regulatory transcript termination regions may be provided in DNA constructs of this invention as well. Transcript termination regions may be provided by the DNA sequence encoding the plant kappa hydroxylase or a convenient transcription termination region derived from a different gene source, for example, the transcript termination region which is naturally associated with the transcript initiation region. Where the transcript termination region is from a different gene source, it will contain at least about 0.5 kb, preferably about 1–3 kb of sequence 3' to the structural gene from which the termination region is derived.

Plant expression or transcription constructs having a plant kappa hydroxylase as the DNA sequence of interest for increased or decreased expression thereof may be employed with a wide variety of plant life, particularly, plant life involved in the production of vegetable oils for edible and industrial uses. Most especially preferred are temperate oilseed crops. Plants of interest include, but are not limited to rapeseed (Canola and high erucic acid varieties), Crambe, Brassica juncea, Brassica nigra, meadowfoam, flax, sunflower, safflower, cotton, Cuphea, soybean, peanut, coconut and oil palms and corn. An important criterion in the selection of suitable plants for the introduction on the kappa hydroxylase is the presence in the host plant of a suitable substrate for the hydroxylase. Thus, for example, production of ricinoleic acid will be best accomplished in plants that normally have high levels of oleic acid in seed lipids. Similarly, production of lesquerolic acid will best be accomplished in plants that have high levels of icosenoic acid in seed lipids.

Depending on the method for introducing the recombinant constructs into the host cell, other DNA sequences may be required. Importantly, this invention is applicable to dicotyledons and monocotyledons species alike and will be readily applicable to new and/or improved transformation and regulation techniques. The method of transformation is not critical to the current invention; various methods of plant transformation are currently available. As newer methods are available to transform crops, they may be directly applied hereunder. For example, many plant species naturally susceptible to Agrobacterium infection may be successfully transformed via tripartite or binary vector methods of Agrobacterium mediated transformation. In addition, techniques of microinjection, DNA particle bombardment, electroporation have been developed which allow for the transformation of various monocot and dicot plant species.

In developing the DNA construct, the various components of the construct or fragments thereof will normally be inserted into a convenient cloning vector which is capable of replication in a bacterial host, e.g., E. coli. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the DNA construct will be a structural gene having the necessary regulatory regions for expression in a host and providing for selection of transformant cells. The gene may provide for resistance to a cytotoxic agent, e.g., antibiotic, heavy metal, toxin, etc., complementation providing prototropy to an auxotrophic host, viral immunity or the like. Depending upon the number of different host species the expression construct or components thereof are introduced, one or more markers may be employed, where different conditions for selection are used for the different hosts.

It is noted that the degeneracy of the DNA code provides that some codon substitutions are permissible of DNA sequences without any corresponding modification of the amino acid sequence.

As mentioned above, the manner in which the DNA construct is introduced into the plant host is not critical to this invention. Any method which provides for efficient transformation may be employed. Various methods for plant cell transformation include the use of Ti- or Ri-plasmids, microinjection, electroporation, infiltration, imbibition, DNA particle bombardment, liposome fusion, DNA bombardment or the like. In many instances, it will be desirable to have the construct bordered on one or both sides of the T-DNA, particularly having the left and right borders, more particularly the right border. This is particularly useful when the construct uses A. tumefaciens or A. rhizogenes as a mode for transformation, although the T-DNA borders may find use with other modes of transformation.

Where Agrobacterium is used for plant cell transformation, a vector may be used which may be introduced into the Agrobacterium host for homologous recombination with T-DNA or the Ti- or Ri-plasmid present in the Agrobacterium host. The Ti- or Ri-plasmid containing the T-DNA for recombination may be armed (capable of causing gall formation) or disarmed (incapable of causing gall), the latter being permissible, so long as the vir genes are present in the transformed Agrobacterium host. The armed plasmid can give a mixture of normal plant cells and gall.

In some instances where Agrobacterium is used as the vehicle for transforming plant cells, the expression construct bordered by the T-DNA border(s) will be inserted into a broad host spectrum vector, there being broad host spectrum vectors described in the literature. Commonly used is pRK2 or derivatives thereof. See, for example, Ditta et al., (1980), which is incorporated herein by reference. Included with the expression construct and the T-DNA will be one or more markers, which allow for selection of transformed Agrobacterium and transformed plant cells. A number of markers have been developed for use with plant cells, such as resistance to kanamycin, the aminoglycoside G418, hygromycin, or the like. The particular marker employed is not essential to this invention, one or another marker being preferred depending on the particular host and the manner of construction.

For transformation of plant cells using Agrobacterium, explants may be combined and incubated with the transformed Agrobacterium for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

The invention now being generally described, it will be more readily understood by reference to the following examples which are included for purposes of illustration only and are not intended to limit the present invention.

EXAMPLES

In the experimental disclosure which follows, all temperatures are given in degrees centigrade (°), weights are given in grams (g), milligram (mg) or micrograms ($\mu$g), concentrations are given as molar (M), millimolar (mM) or micromolar ($\mu$M) and all volumes are given in liters (l), microliters ($\mu$l) or milliliters (ml), unless otherwise indicated.

Example 1

Production of Novel Hydroxylated Fatty Acids in Arabidopsis Thaliana Arabudiopsis Thaliana Overview The kappa hydroxylase encoded by the previously described fah12 gene from Castor (U.S. patent application Ser. No. 08/320,982) was used to produce ricinoleic acid, lesquerolic acid, densipolic acid and auricolic acid in transgenic Arabidopsis plants. This example reduces to practice the method taught in Example 2 of the foregoing application.

Production of Transgenic Plants

A variety of methods have been developed to insert a DNA sequence of interest into the genome of a plant host to obtain the transcription and translation of the sequence to effect phenotypic changes. The following methods represent only one of many equivalent means of producing transgenic plants and causing expression of the hydroxylase gene.

Arabidopsis plants were transformed, by Agrobacterium-mediated transformation, with the kappa hydroxylase encoded by the Castor fah12 gene on binary Ti plasmid pB6. This plasmid was previously used to transform Nicotiana tabacum for the production of ricinoleic acid (U.S. patent application 08/320,982).

Inoculums of Agrobacterium tumefaciens strain GV3101 containing binary Ti plasmid pB6 were plated on L-broth plates containing 50 $\mu$g/ml kanamycin and incubated for 2 days at 30° C. Single colonies were used to inoculate large liquid cultures (L-broth medium with 50 mg/l rifampicin, 110 mg/l gentamycin and 200 mg/l kanamycin) to be used for the transformation of Arabidopsis plants.

Arabidopsis plants were transformed by the in planta transformation procedure essentially as described by Bechtold et al., (1993). Cells of A. tumefaciens GV3101(pB6) were harvested from liquid cultures by centrifugation, then resuspended in infiltration medium at $OD_{600}$=0.8 (Infiltration medium was Murashige and Skoog macro and micronutrient medium (Sigma Chemical Co., St. Louis, Mo.) containing 10 mg/l 6-benzylaminopurine and 5% glucose). Batches of 12–15 plants were grown for 3 to 4 weeks in natural light at a mean daily temperature of approximately 25° C. in 3.5 inch pots containing soil. The intact plants were immersed in the bacterial suspension then transferred to a vacuum chamber and placed under 600 mm of vacuum produced by a laboratory vacuum pump until tissues appeared uniformly water-soaked (approximately 10 min). The plants were grown at 25° C. under continuous light (100 $\mu$mol m$^{-2}$ s$^{-1}$ irradiation in the 400 to 700 nm range) for four weeks. The seeds obtained from all the plants in a pot were harvested as one batch. The seeds were sterilized by sequential treatment for 2 min with ethanol followed by 10 min in a mixture of household bleach (Chlorox), water and Tween-80 (50%, 50%, 0.05%) then rinsed thoroughly with sterile water. The seeds were plated at high density (2000 to 4000 per plate) onto agar-solidified medium in 100 mm petri plates containing ½ X Murashige and Skoog salts medium enriched with B5 vitamins (Sigma Chemical Co., St. Louis, Mo.) and containing kanamycin at 50 mg/l. After incubation for 48 h at 4° C. to stimulate germination, seedlings were grown for a period of seven days until transformants were clearly identifiable as healthy green seedlings against a background of chlorotic kanamycin-sensitive seedlings. The transformants were transferred to soil for two weeks before leaf tissue could be used for DNA and lipid analysis. More than 20 transformants were obtained.

DNA was extracted from young leaves from transformants to verify the presence of an intact fah12 gene. The presence of the transgene in a number of the putative transgenic lines was verified by using the polymerase chain reaction to amplify the insert from pB6. The primers used were HF2=GCTCTTTTGTGCGCTCATTC (SEQ ID NO:12) and HR1=CGGTACCAGAAAACGCCTTG (SEQ ID NO:13), which were designed to allow the amplification of a 700 bp fragment. Approximately 100 ng of genomic DNA was added to a solution containing 25 pmol of each primer, 1.5 U Taq polymerase (Boehringer Manheim), 200 uM of dNTPs, 50 mM KCl, 10 mM Tris.Cl (pH 9), 0.1% (v/v) Triton X-100, 1.5 mM $MgCl_2$, 3% (v/v) formamide, to a final volume of 50 μl. Amplifications conditions were: 4 min denaturation step at 94° C., followed by 30 cycles of 92° C. for 1 min, 55° C. for 1 min, 72° C. for 2 min. A final extension step closed the program at 72° C. for 5 min. Transformants could be positively identified after visualization of a characteristic 1 kb amplified fragment on an ethidium bromide stained agarose gel. All transgenic lines tested gave a PCR product of a size consistent with the expected genotype, confirming that the lines were, indeed, transgenic. All further experiments were done with three representative transgenic lines of the wild type designated as 1-3, 4D, 7-4 and one transgenic line of the fad2 mutant line JB12. The transgenic JB12 line was included in order to test whether the increased accumulation of oleic acid in this mutant would have an effect on the amount of ricinoleic acid that accumulated in the transgenic plants.

Analysis of Transgenic Plants

Leaves and seeds from fah12 transgenic Arabidopsis plants were analyzed for the presence of hydroxylated fatty acids using gas chromatography. Lipids were extracted from 100–200 mg leaf tissue or 50 seeds. Fatty acid methyl esters (FAMES) were prepared by placing tissue in 1.5 ml of 1.0 M methanolic HCl (Supelco Co.) in a 13×100 mm glass screw-cap tube capped with a teflon-lined cap and heated to 80° C. for 2 hours. Upon cooling, 1 ml petroleum ether was added and the FAMES removed by aspirating off the ether phase which was then dried under a nitrogen stream in a glass tube. One hundred μl of N,O-bis(Trimethylsilyl) trifluoroacetamide (BSTFA; Pierce Chemical Co) and 200 μl acetonitrile was added to derivatize the hydroxyl groups. The reaction was carried out at 70° C. for 15 min. The products were dried under nitrogen, redissolved in 100 μl chloroform and transferred to a gas chromatograph vial. Two μl of each sample were analyzed on a SP2340 fused silica capillary column (30 m, 0.75 mm ID, 0.20 mm film, Supelco), using a Hewlett-Packard 5890 II series Gas Chromatograph. The samples were not split, the temperature program was 195° C. for 18 min, increased to 230° C. at 25° C./min, held at 230° C. for 5 min then down to 195° C. at 25° C./min., and flame ionization detectors were used.

The chromatographic elution time of methyl esters and O-TMS derivatives of ricinoleic acid, lesquerolic acid and auricolic acid was established by GC-MS of lipid samples from seeds of L. fendleri and comparison to published chromatograms of fatty acids from this species (Carlson et al., 1990). A O-TMS-methyl-ricinoleate standard was prepared from ricinoleic acid obtained from Sigma Chemical Co (St, Louis, Mo.). O-TMS-methyl-lesqueroleate and O-TMS-methyl-auricoleate standards were prepared from triacylglycerols purified from seeds of L. fendleri. The mass spectrum of O-TMS-methyl-ricinoleate, O-TMS-methyl-densipoleate, O-TMS-methyl-lesqueroleate, and O-TMS-methyl-auricoleate are shown in FIGS. 1A–D, respectively. The structures of the characteristic ions produced during mass spectrometry of these derivatives are shown in FIG. 2.

Figure 3A:
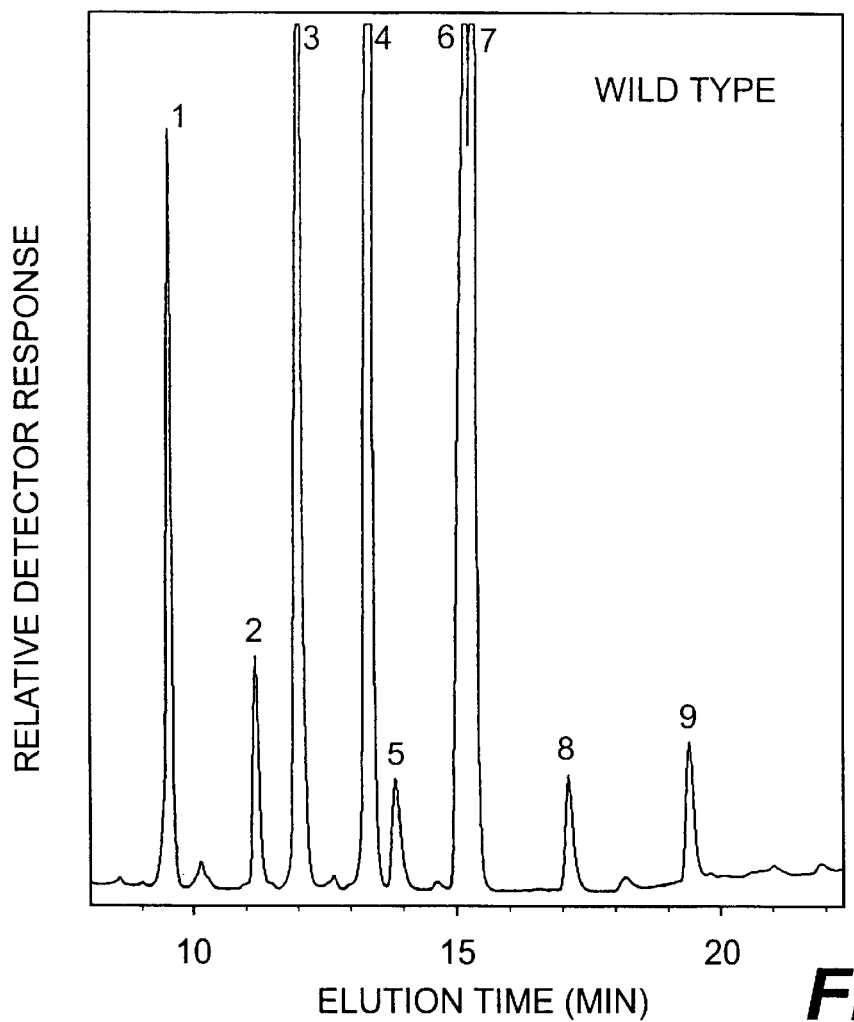
FIG. 3A shows the gas chromatogram of fatty acids extracted from seeds of wild type Arabidopsis plants.
Figure 3B:
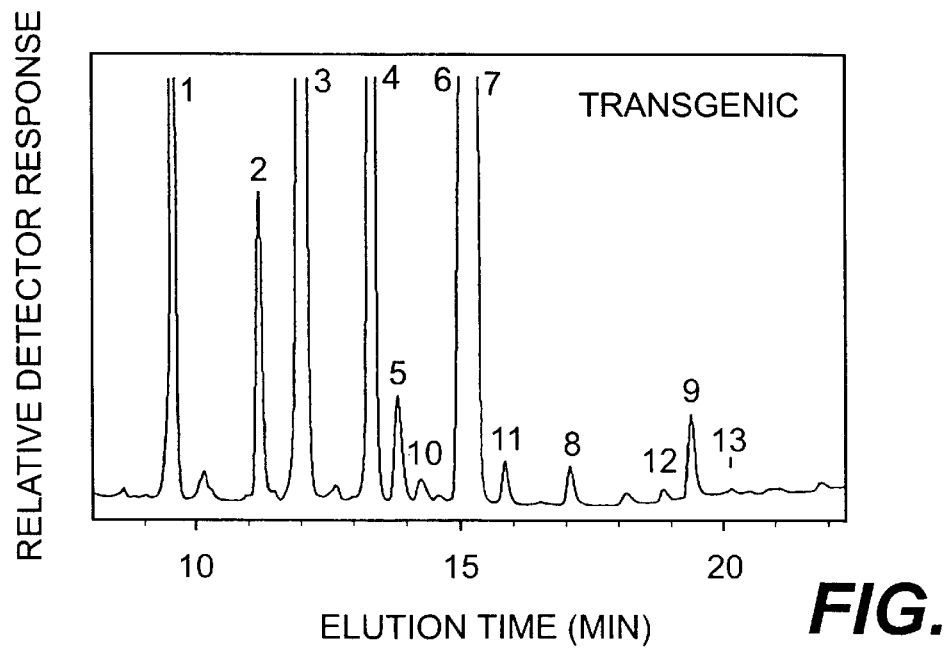
FIG. 3B shows the gas chromatogram of fatty acids extracted from seeds of transgenic Arabidopsis plants containing the fah12 hydroxylase gene. The numbers indicate the following fatty acids: [1] 16:0; [2] 18:0; [3] 18:1cisΔ9; [4] $18:2^{cis\Delta9,12}$; [5] 20:0; [6] $20:1^{cis\Delta11}$; [7] $18:3^{cis\Delta9,12,15}$; [8] $20:2^{cis\Delta11,14}$; [9] $22:1^{cis\Delta13}$; [10] ricinoleic acid; [11] densipolic acid; [12] lesquerolic acid; [13] auricolic acid.
Figure 4A:
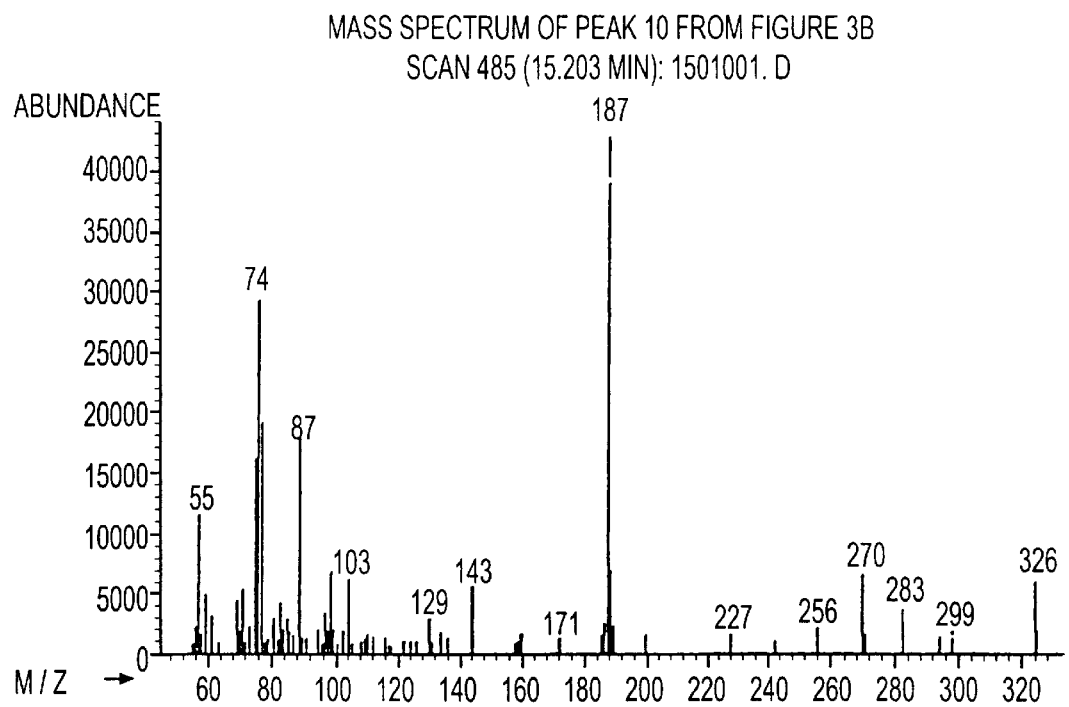
FIGS. 4A–D show the mass spectra of novel fatty acids found in seeds of transgenic plants.
Figure 4B:
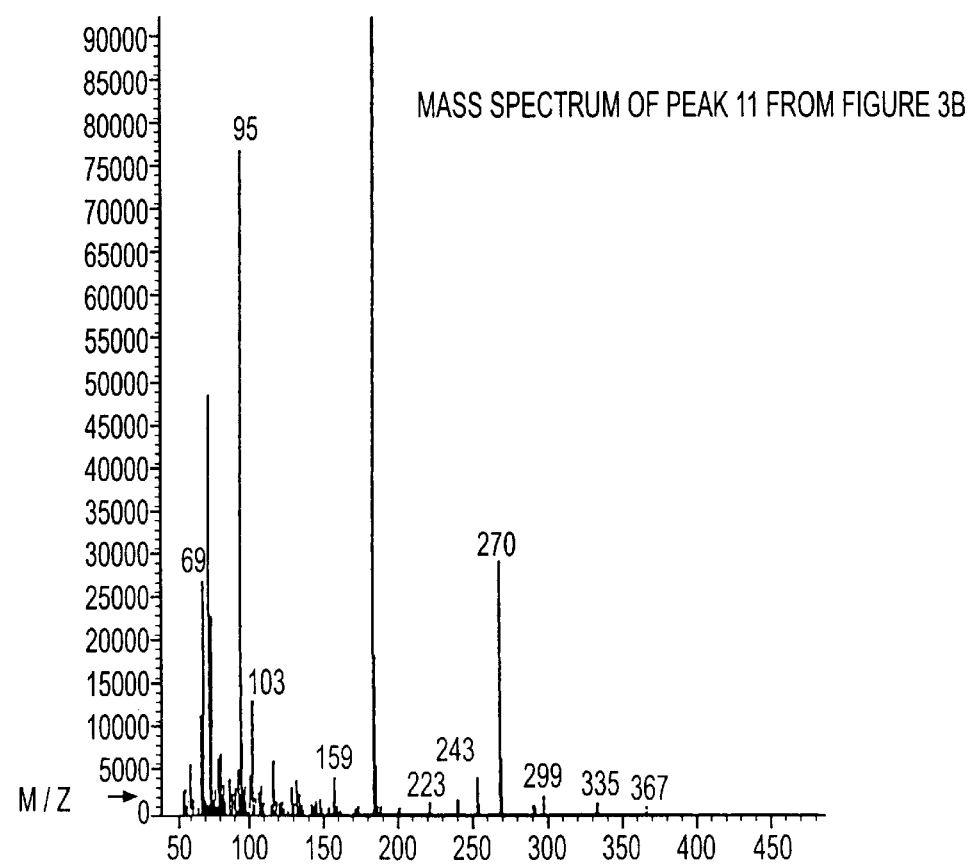
Figure 4C:
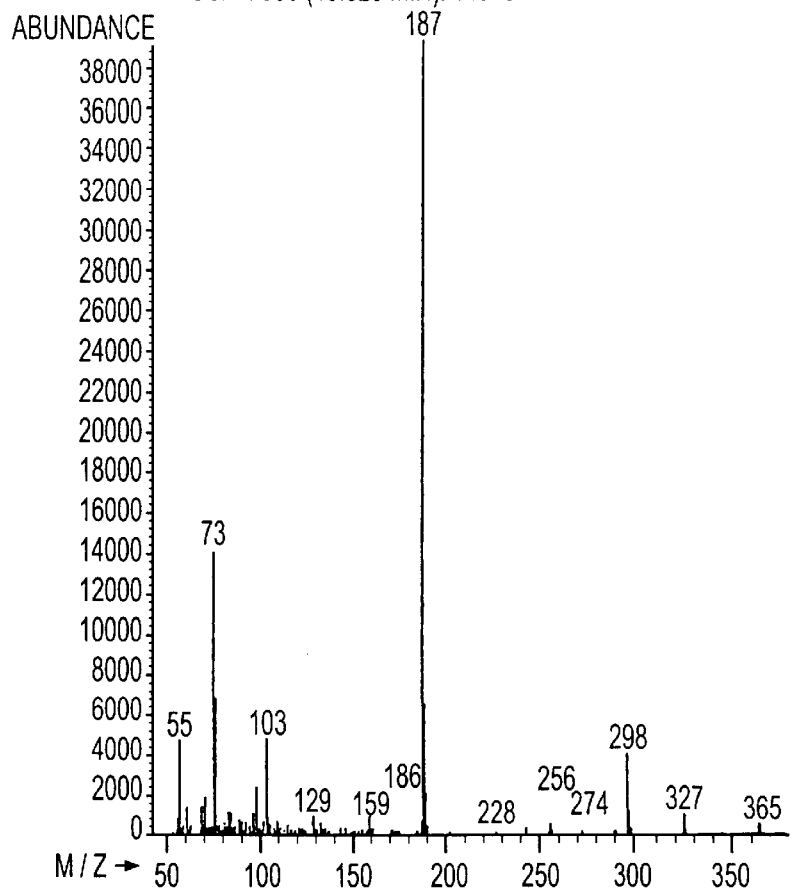
Figure 4D:
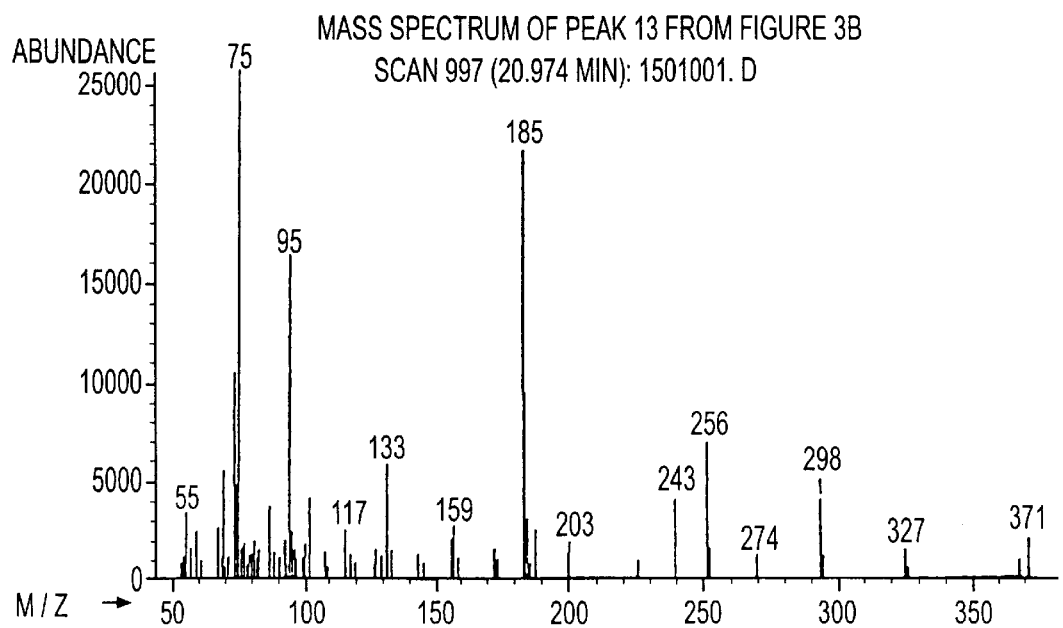

Lipid extracted from transgenic tissues were analyzed by gas chromatography and mass spectrometry for the presence of hydroxylated fatty acids. As a matter of reference, the average fatty acid composition of leaves in Arabidopsis wild type and fad2 mutant lines was reported by Miquel and Browse (1992). Gas chromatograms of methylated and silylated fatty acids from seeds of wild type and a fah12 transgenic wild type plant are shown in FIGS. 3A and 3B, respectively. The profiles are very similar except for the presence of three small but distinct peaks at 14.3, 15.9 and 18.9 minutes. A very small peak at 20.15 min was also evident. The elution time of the peaks at 14.3 and 18.9 min corresponded precisely to that of comparably prepared ricinoleic and lesquerolic standards, respectively. No significant differences were observed in lipid extracts from leaves or roots of the wild type and the fah12 transgenic wild type lines (Table 1). Thus, in spite of the fact that the fah12 gene is expressed throughout the plant, we observed effects on fatty acid composition only in seed tissue. A similar observation was described previously for transgenic fah12 tobacco in patent application No. 08/320,982.

TABLE 1

Fatty acid composition of lipids from transgenic and wild type Arabidopsis. The values are the means obtained from analysis of samples from three Independent transgenic lines, or three independent samples of wild type and fad2 lines.

| Fatty acid | Seed | | | | Leaf | | Root | |
|---|---|---|---|---|---|---|---|---|
| | WT | FAH12/WT | FAH12/fad2 | JB12 | WT | FAH12/WT | WT | FAH12/WT |
| 16:0 | 8.5 | 8.2 | 6.4 | 6.1 | 16.5 | 17.5 | 23.9 | 24.9 |
| 16:3 | 0 | 0 | 0 | 0 | 10.1 | 9.8 | 0 | 0 |
| 18:0 | 3.2 | 3.5 | 2.9 | 3.5 | 1.3 | 1.2 | 2.0 | 1.9 |
| 18:1 | 15.4 | 26.3 | 43.4 | 47.8 | 2.4 | 3.4 | 5.4 | 3.2 |
| 18:2 | 27.0 | 21.4 | 10.2 | 7.2 | 15.1 | 14.0 | 32.2 | 29.4 |
| 18:3 | 22.0 | 16.6 | — | 9.7 | 36.7 | 36.0 | 26.7 | 30.6 |
| 20:1 | 14.0 | 14.3 | — | 13.1 | 0 | 0 | 0 | 0 |
| 22:1 | 2.0 | 1.0 | 0.5 | 0.5 | 0 | 0 | 0 | 0 |
| 24:1 | 2.5 | 1.7 | 2.0 | 1.6 | 0 | 0 | 0 | 0 |
| 18:1-OH | 0 | 0.4 | 0.3 | 0 | 0 | 0 | 0 | 0 |

TABLE 1-continued

Fatty acid composition of lipids from transgenic and wild type Arabidopsis. The values are the means obtained from analysis of samples from three Independent transgenic lines, or three independent samples of wild type and fad2 lines.

| Fatty acid | Seed | | | | Leaf | | Root | |
|---|---|---|---|---|---|---|---|---|
| | WT | FAH12/WT | FAH12/fad2 | JB12 | WT | FAH12/WT | WT | FAH12/WT |
| 18:2-OH | 0 | 0.4 | 0.3 | 0 | 0 | 0 | 0 | 0 |
| 20:1-OH | 0 | 0.2 | 0.1 | 0 | 0 | 0 | 0 | 0 |
| 20:2-OH | 0 | 0.1 | 0.1 | 0 | 0 | 0 | 0 | 0 |

In order to confirm that the observed new peaks in the transgenic lines corresponded to derivatives of ricinoleic, lesquerolic, densipolic and auricolic acids, mass spectrometry was used. The fatty acid derivatives were resolved by gas chromatography as described above except that a Hewlett-Packard 5971 series mass selective detector was used in place of the flame ionization detector used in the previous experiment. The spectra of the four new peaks in FIG. 3B (peak numbers 10, 11, 12 and 13) are shown in FIGS. 4A–D, respectively. Comparison of the spectrum obtained for the standards with that obtained for the four peaks from the transgenic lines confirms the identity of the four new peaks. On the basis of the three characteristic peaks at M/Z 187, 270 and 299, peak 10 is unambiguously identified as O-TMS-methylricinoleate. On the basis of the three characteristic peaks at M/Z 185, 270 and 299, peak 11 is unambiguously identified as O-TMS-methyldensipoleate. On the basis of the three characteristic peaks at M/Z 187, 298 and 327, peak 12 is unambiguously identified as O-TMS-methyllesqueroleate. On the basis of the three characteristic peaks at M/Z 185, 298 and 327, peak 13 is unambiguously identified as O-TMS-methylauricoleate. These results unequivocally demonstrate the identity of the fah12 cDNA as encoding a hydroxylase that hydroxylates both oleic acid to produce ricinoleic acid and also hydroxylate icosenoic acid to produce lesquerolic acid. These results also provide additional evidence that the hydroxylase can be functionally expressed in a heterologous plant species in such a way that the enzyme is catalytically functional. These results also demonstrate that expression of this hydroxylase gene leads to accumulation of ricinoleic, lesquerolic, densipolic and auricolic acids in a plant species that does not normally accumulate hydroxylated fatty acids in extractable lipids.

The presence of lesquerolic acid in the transgenic plants was anticipated in the previous patent application (No. 08/320,982) based on the biochemical evidence suggesting broad substrate specificity of the kappa hydroxylase. By contrast, the accumulation of densipolic and auricolic acids was less predictable. Since Arabidopsis does not normally contain significant quantities of the non-hydroxylated precursors of these fatty acids which could serve as substrates for the hydroxylase, it appears that one or more of the three n-3 fatty acid desaturases known in Arabidopsis (eg., fad3, fad7, fad8; reviewed in Gibson et al., 1995) are capable of desaturating the hydroxylated compounds at the n-3 position. That is, densipolic acid is produced by the action of an n-3 desaturase on ricinoleic acid. Auricolic acid is produced by the action of an n-3 desaturase on lesquerolic acid. Because it is located in the endoplasmic reticulum, the fad3 desaturase is almost certainly responsible. This can be tested in the future by producing fah12-containing transgenic plants of the fad3-deficient mutant of Arabidopsis (similar experiments can be done with fad7 and fad8). It is also formally possible that the enzymes that normally elongate $18:1^{cis\ \Delta 9}$ to $20:1^{cis\ \Delta 11}$ may elongate $12OH\text{-}18:1^{cis\ \Delta 9}$ to $14OH\text{-}20:1^{cis\ \Delta 11}$, and $12OH\text{-}18:2^{cis\ \Delta 9,15}$ to $14OH\text{-}20:2^{cis\ \Delta 11,17}$.

The amount of the various fatty acids in seed, leaf and root lipids of the control and transgenic plants is presented in Table 1. Although the amount of hydroxylated fatty acids produced in this example is less than desired for commercial production of ricinoleate and other hydroxylated fatty acids from plants, we envision numerous improvements of this invention that will increase the level of accumulation of hydroxylated fatty acids in plants that express the fah12 or related hydroxylase genes. Improvements in the level and tissue specificity of expression of the hydroxylase gene is envisioned. Methods to accomplish this by the use of strong, seed-specific promoters such as the *B. napus* napin promoter or the native promoters of the castor fah12 gene or the corresponding hydroxylase gene from *L. fendleri* will be obvious to one skilled in the art. Additional improvements are envisioned to involve modification of the enzymes which cleave hydroxylated fatty acids from phosphatidylcholine, reduction in the activities of enzymes which degrade hydroxylated fatty acids and replacement of acyltransferases which transfer hydroxylated fatty acids to the sn-1, sn-2 and sn-3 positions of glycerolipids. Although genes for these enzymes have not been described in the scientific literature, their utility in improving the level of production of hydroxylated fatty acids can be readily envisioned based on the results of biochemical investigations of ricinoleate synthesis.

Although Arabidopsis is not an economically important plant species, it is widely accepted by plant biologists as a model for higher plants. Therefore, the inclusion of this example is intended to demonstrate the general utility of the invention described here and in the previous application (No. 08/320,982) to the modification of oil composition in higher plants. One advantage of studying the expression of this novel gene in Arabidopsis is the existence in this system of a large body of knowledge on lipid metabolism, as well as the availability of a collection of mutants which can be used to provide useful information on the biochemistry of fatty acid hydroxylation in plant species. Another advantage is the ease of transposing any of the information obtained on metabolism of ricinoleate in Arabidopsis to closely related species such as the crop plants Brassica napus, *Brassica juncea* or *Crambe abyssinica* in order to mass produce ricinoleate, lesqueroleate or other hydroxylated fatty acids for industrial use. The kappa hydroxylase is useful for the production of ricinoleate or lesqueroleate in any plant species that accumulates significant levels of the precursors, oleic acid and icosenoic acid. Of particular interest are genetically modified varieties that accumulate high levels of oleic acid. Such varieties are currently available for sunflower and Canola. Production of lesquerolic acid and related hydroxy fatty acids can be achieved in species that accumulate high levels of icosenoic acid or other long chain monoenoic acids. Such plants may in the future be produced by genetic engineering of plants that do not normally make such precursors. Thus, we envision that the use of the kappa hydroxylase is of general utility.

Example 2

Isolation of Lesquerella Kappa Hydroxylase Genomic Clone

Overview

Regions of nucleotide sequence that were conserved in both the Castor kappa hydroxylase and the Arabidopsis fad2 Δ12 fatty acid desaturase were used to design oligonucleotide primers. These were used with genomic DNA from *Lesquerella fendleri* to amplify fragments of several homologous genes. These amplified fragments were then used as hybridization probes to identify full length genomic clones from a genomic library of *L. fendleri*. Hydroxylated fatty acids are specific to the seed tissue of Lesquerella sp., and are not found to any appreciable extent in vegetative tissues. One of the two genes identified by this method was expressed in both leaves and developing seeds and is therefore thought to correspond to the Δ12 fatty acid desaturase. The other gene was expressed at high levels in developing seeds but was not expressed or was expressed at very low levels in leaves and is the kappa hydroxylase from this species. The identity of this gene will be established by introducing the gene into transgenic Arabidopsis plants and showing that it causes the accumulation of ricinoleic acid, lesquerolic acid, densipolic acid and auricolic acid in seed lipids. The promoter of this gene is also of utility because it is able to direct expression of a gene specifically in developing seeds at a time when storage lipids are accumulating. This promoter is, therefore, of great utility for many applications in the genetic engineering of seeds, particularly in members of the Brassicacea.

The various steps involved in this process are described in detail below. Unless otherwise indicated, routine methods for manipulating nucleic acids, bacteria and phage were as described by Sambrook et al. (1989).

Isolation of a Fragment of the Lesauerella Kappa Hydroxylase Gene

Oligonucleotide primers for the amplification of the *L. fendleri* kappa hydroxylase were designed by choosing regions of high deduced amino acid sequence homology between the Castor kappa hydroxylase and the Arabidopsis Δ12 desaturase (fad2). Because most amino acids are encoded several different codons, these oligonucleotides were designed to encode all possible codons that could encode the corresponding amino acids. The sequence of these mixed oligonucleotides was:
Oligo 1: TAYWSNCAYMGNMGNCAYCA (SEQ ID NO:14)
Oligo 2: RTGRTGNGCNACRTGNGTRTC (SEQ ID NO:15)
(Where: Y=C+T; W=A+T; S=G+C; N=A+G+C+T; M=A+C; R=A+G)

These oligonucleotides were used to amplify a fragment of DNA from *L. fendleri* genomic DNA by the polymerase chain reaction (PCR) using the following conditions: Approximately 100 ng of genomic DNA was added to a solution containing 25 pmol of each primer, 1.5 U Taq polymerase (Boehringer Manheim), 200 uM of dNTPs, 50 mM KCl, 10 mM Tris.Cl (pH 9), 0.1% (v/v) Triton X-100, 1.5 mM $MgCl_2$, 3% (v/v) formamide, to a final volume of 50 μl. Amplifications conditions were: 4 min denaturation step at 94° C., followed by 30 cycles of 92° C. for 1 min, 55° C. for 1 min, 72° C. for 2 min. A final extension step closed the program at 72° C. for 5 min.

PCR products of approximately 540 bp were observed following electrophoretic separation of the products of the PCR reaction in agarose gels. Two of these fragments were cloned into pBluescript (Stratagene) to give rise to plasmids pLesq2 and pLesq3. The sequence of the inserts in these two plasmids was determined by the chain termination method. The sequence of the insert in pLesq2 is presented as FIG. 5 (SEQ ID NO:1) and the sequence of the insert in pLesq3 is presented as FIG. 6 (SEQ ID NO:2). The high degree of sequence identity between the two clones indicated that they were both potential candidates to be either a Δ12 desaturase or a kappa hydroxylase.

Northern Analysis

In *L. fendleri*, hydroxylated fatty acids are found in large amounts in seed oils but are not found in appreciable amounts in leaves. Therefore, an important criterion in discriminating between a fatty acyl desaturase and kappa hydroxylase is that the kappa hydroxylase gene is expected to be expressed more highly in tissues which have high level of hydroxylated fatty acids than in other tissues whereas all plant tissues should contain mRNA for an ω6 fatty acyl desaturase since diunsaturated fatty acids are found in the lipids of all tissues in most or all plants. Therefore, it was of great interest to determine whether the gene corresponding to pLesq2 was also expressed only in seeds, or is also expressed in other tissues. This question was addressed by testing for hybridization of pLesq2 to RNA purified from developing seeds and from leaves.

Total RNA was purified from developing seeds and young leaves of *L. fendleri* using an Rneasy RNA extraction kit (Qiagen), according to the manufacturer's instructions. RNA concentrations were quantified by UV spectrophotometry at λ=260 and 280 nm. In order to ensure even loading of the gel to be used for Northern blotting, RNA concentrations were further adjusted after recording fluorescence under UV light of RNA samples stained with ethidium bromide and run on a test denaturing gel.

Total RNA prepared as described above from leaves and developing seeds was electrophoresed through an agarose gel containing formaldehyde (Iba et al., 1993). An equal quantity (10 μg) of RNA was loaded in both lanes, and RNA standards (0.16–1.77 kb ladder, Gibco-BRL) were loaded in a third lane. Following electrophoresis, RNA was transferred from the gel to a nylon membrane (Hybond N+, Amersham) and fixed to the filter by exposure to UV light. A ⁻P-labelled probe was prepared from insert DNA of clone pLesq2 by random priming and hybridized to the membrane overnight at 52° C., after it had been prehybridized for 2 h. The prehybridization solution contained 5×SSC, 10×Denhardt's solution, 0.1% SDS, 0.1M $KPO_4$ pH 6.8, 100 μg/ml salmon sperm DNA. The hybridization solution had the same basic composition, but no SDS, and it contained 10% dextran sulfate and 30% formamide. The blot was washed once in 2×SSC, 0.5% SDS at 65° C. then in 1×SSC at the same temperature.

Figure 7:
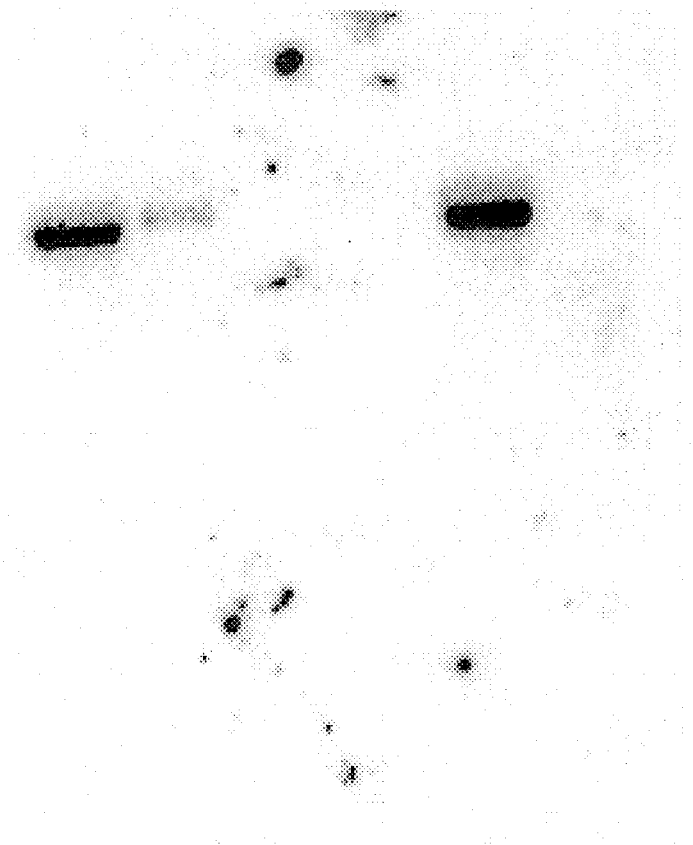
FIG. 7 shows a Northern blot of total RNA from seeds of L. fendleri probed with pLesq2 or pLesq3. S, indicates RNA is from seeds; L, indicates RNA is from leaves.

Brief (30 min) exposure of the blot to X-ray film revealed that the probe pLesq2 hybridized to a single band only in the seed RNA lane (FIG. 7). The blot was re-probed with the insert from pLesq3 gene, which gave bands of similar intensity in the seed and leaf lanes (FIG. 7).

These results show that the gene corresponding to the clone pLesq2 is highly and specifically expressed in seed of *L. fendleri*. In conjunction with knowledge of the nucleotide and deduced amino acid sequence, strong seed-specific expression of the gene corresponding to the insert in pLesq2 is a convincing indicator of the role of the enzyme in synthesis of hydroxylated fatty acids in the seed oil.

Characterization of a Genomic Clone of the Kappa Hydroxylase

Genomic DNA was prepared from young leaves of *L. fendleri* as described by Murray and Thompson (1980). A Sau3AI-partial digest genomic library constructed in the vector λDashII (Stratagene, 11011 North Torrey Pines Road, La Jolla Calif. 92037) was prepared by partially digesting 500 µg of DNA, size-selecting the DNA on a sucrose gradient (Sambrook et al., 1989), and ligating the DNA (12 kb average size) to the BamHI-digested arms of µDashII. The entire ligation was packaged according to the manufacturer's conditions and plated on *E. coli* strain XL1-Blue MRA-P2 (Stratagene). This yielded $5 \times 10^5$ primary recombinant clones. The library was then amplified according to the manufacturer's conditions. A fraction of the genomic library was plated on *E. coli* XL1-Blue and resulting plaques (150,000) were lifted to charged nylon membranes (Hybond N+, Amersham), according to the manufacturer's conditions. DNA was crosslinked to the filters under UV in a Stratalinker (Stratagene).

Several clones carrying genomic sequences corresponding to the *L. fendleri* hydroxylase were isolated by probing the membranes with the insert from pLesq2 that was PCR-amplified with internal primers and labelled with $^{32}$P by random priming. The filters were prehybridized for 2 hours at 65° C. in 7% SDS, 1 mM EDTA, 0.25 M Na$_2$HPO$_4$ (pH 7.2), 1% BSA and hybridized to the probe for 16 hours in the same solution. The filters were sequentially washed at 65° C. in solutions containing 2×SSC, 1×SSC, 0.5×SSC in addition to 0.1 % SDS. A 2.6 kb Xba I fragment containing the complete coding sequence for the kappa-hydroxylase and approximately 1 kb of the 5' upstream region was subcloned into the corresponding site of pBluescript KS to produce plasmid pLesq-Hyd and the sequence determined completely using an automatic sequencer by the dideoxy chain termination method. Sequence data was analyzed using the program DNASIS (Hitachi company).

The sequence of the insert in clone pLesq-Hyd is shown in FIGS. 8A–B. The sequence entails 1855 bp of contiguous DNA sequence (SEQ ID NO:3). The clone encodes a 401 bp 5' untranslated region (i.e., nucleotides preceding the first ATG codon), an 1152 bp open reading frame, and a 302 bp 3' untranslated region. The open reading frame encodes a 384 amino acid protein with a predicted molecular weight of 44,370 (SEQ ID NO:4). The amino terminus lacks features of a typical signal peptide (von Heijne, 1985).

The exact translation-initiation methionine has not been experimentally determined, but on the basis of deduced amino acid sequence homology to the Castor kappa hydroxylase (noted below) is thought to be the methionine encoded by the first ATG codon at nucleotide 402.

Comparison of the pLesq-Hyd deduced amino acid sequence with sequences of membrane-bound desaturases and the castor hydroxylase (FIGS. 9A–B) indicates that pLesq-Hyd is homologous to these genes. This figure shows an alignment of the *L. fendleri* hydroxylase (SEQ ID NO:4) with the castor hydroxylase (van de Loo et al. 1995), the Arabidopsis fad2 cDNA which encodes an endoplasmic reticulum-localized Δ12 desaturase (called fad2) (Okuley et al., 1994), two soybean fad2 desaturase clones, a *Brassica napus* fad2 clone, a *Zea mays* fad2 clone and partial sequence of a *R. communis* fad2 clone. The high degree of sequence homology indicates that the gene products are of similar function. For instance, the overall homology between the Lesquerella hydroxylase and the Arabidopsis fad2 desaturase was 92.2% similarity and 84.8% identity and the two sequences differed in length by only one amino acid.

Southern Hybridization

Southern analysis was used to examine the copy number of the genes in the *L. fendleri* genome corresponding to the clone pLesq-Hyd. Genomic DNA (5 µg) was digested with EcoR I, Hind III and Xba I and separated on a 0.9% agarose gel. DNA was alkali-blotted to a charged nylon membrane (Hybond N+, Amersham), according to the manufacturer's protocol. The blot was prehybridized for 2 hours at 65° C. in 7% SDS, 1 mM EDTA, 0.25 M Na$_2$HPO4 (pH 7.2), 1% BSA and hybridized to the probe for 16 hours in the same solution with pLesq-Hyd insert PCR-amplified with internal primers and labelled with $^{32}$P by random priming. The filters were sequentially washed at 65° C. in solutions containing 2×SSC, 1×SSC, 0.5×SSC in addition to 0.1% SDS, then exposed to X-ray film.

Figure 10:
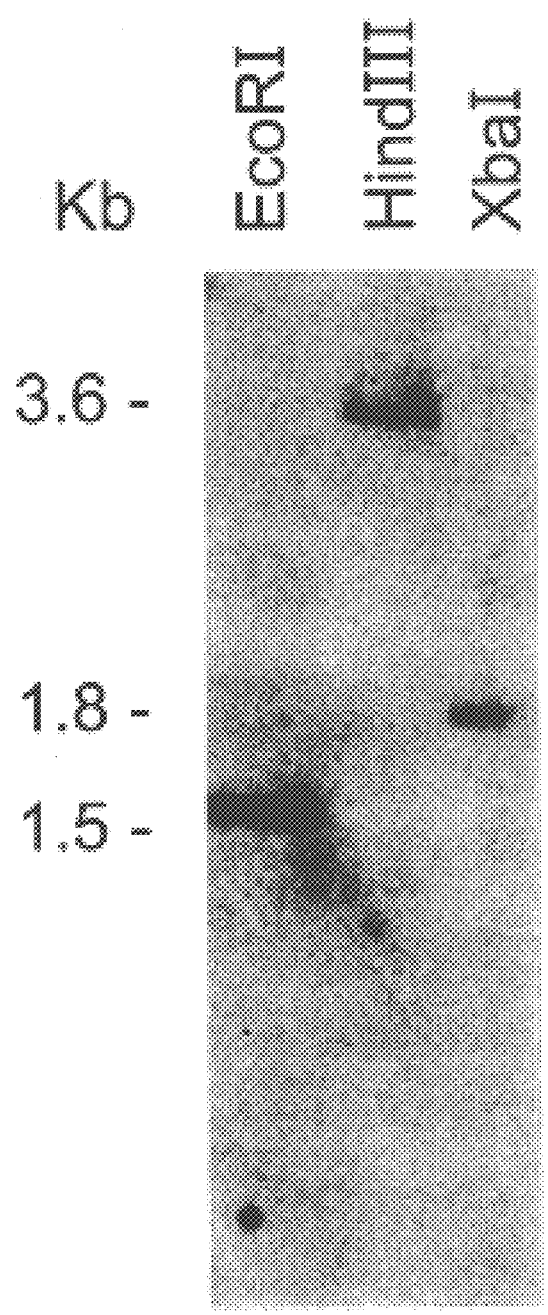
FIG. 10 shows a Southern blot of genomic DNA from L. fendleri probed with pLesq-HYD. E=EcoRI, H =HindIII, X=XbaI.

The probe hybridized with a single band in each digest of *L. fendleri* DNA (FIG. 10), indicating that the gene from which pLesq-Hyd was transcribed is present in a single copy in the *L. fendleri* genome.

Expression of pLesq-Hyd in Transgenic Plants

There are a wide variety of plant promoter sequences which may be used to cause tissue-specific expression of cloned genes in transgenic plants. For instance, the napin promoter and the acyl carrier protein promoters have previously been used in the modification of seed oil composition by expression of an antisense form of a desaturase (Knutson et al. 1992). Similarly, the promoter for the β-subunit of soybean β-conglycinin has been shown to be highly active and to result in tissue-specific expression in transgenic plants of species other than soybean (Bray et al., 1987). Thus, although we describe the use of the *L. fendleri* kappa hydroxylase promoter in the examples described here, other promoters which lead to seed-specific expression may also be employed for the production of modified seed oil composition. Such modifications of the invention described here will be obvious to one skilled in the art.

Figure 11:
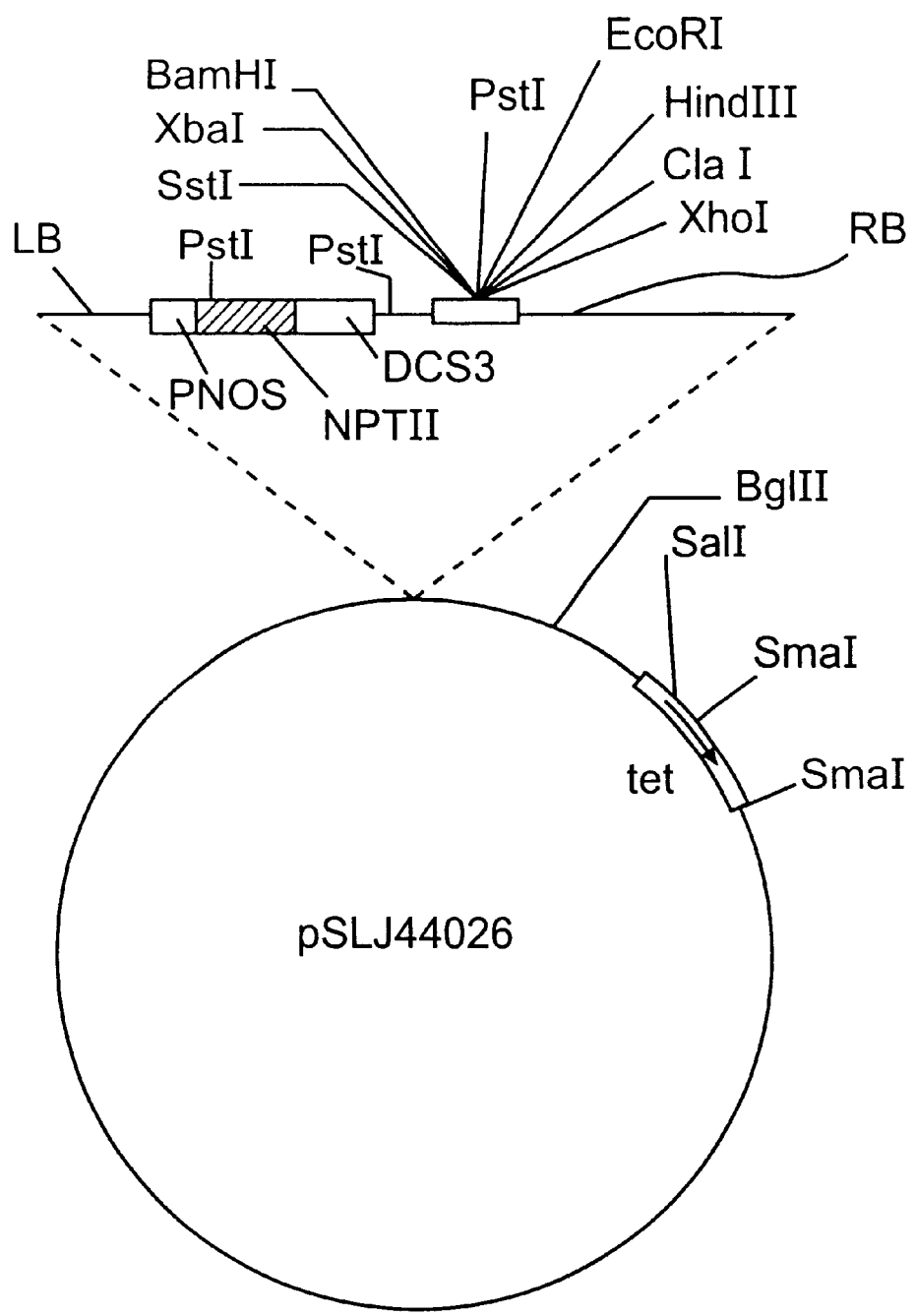
FIG. 11 shows a map of binary Ti plasmid pSLJ44024.

Constructs for expression of *L. fendleri* kappa hydroxylase in plant cells are prepared as follows: A 13 kb SalI fragment containing the pLesq-Hyg gene was ligated into the XhoI site of binary Ti plasmid vector pSLJ44026 (Jones et al., 1992) (FIG. 11) to produce plasmid pTi-Hyd and transformed into *Agrobacterium tumefaciens* strains GV3101 by electroporation. Strain GV3101 (Koncz and Schell, 1986) contains a disarmed Ti plasmid. Cells for electroporation were prepared as follows. GV3101 was grown in LB medium with reduced NaCl (5 g/l). A 250 ml culture was grown to OD$_{600}$=0.6, then centrifuged at 4000 rpm (Sorvall GS-A rotor) for 15 min. The supernatant was aspirated immediately from the loose pellet, which was gently resuspended in 500 ml ice-cold water. The cells were centrifuged as before, resuspended in 30 ml ice-cold water, transferred to a 30 ml tube and centrifuged at 5000 rpm (Sorvall SS-34 rotor) for 5 min. This was repeated three times, resuspending the cells consecutively in 30 ml ice-cold water, 30 ml ice-cold 10% glycerol, and finally in 0.75 ml ice-cold 10% glycerol. These cells were aliquoted, frozen in liquid nitrogen, and stored at −80° C.

Electroporations employed a Biorad Gene pulsar instrument using cold 2 mm-gap cuvettes containing 40 µl cells and 1 µl of DNA in water, at a voltage of 2.5 KV, and 200 Ohms resistance. The electroporated cells were diluted with 1 ml SOC medium (Sambrook et al., 1989, page A 2) and incubated at 28° C. for 2–4 h before plating on medium containing kanamycin (50 mg/l).

Arabidopsis thaliana can be transformed with the Agrobacterium cells containing pTi-Hyd as described in Example 1 above. Similarly, the presence of hydroxylated fatty acids in the transgeneic Arabidopsis plants can be demonstrated by the methods described in Example 1 above.

Constitutive Expression of the L. fendleri Hydroxylase in Transgenic Plants

A 1.5 kb EcoR I fragment from pLesq-Hyg comprising the entire coding region of the hydroxylase was gel purified, then cloned into the corresponding site of pBluescript KS (Stratagene). Plasmid DNA from a number of recombinant clones was then restricted with Pst I, which should cut only once in the insert and once in the vector polylinker sequence. Release of a 920 bp fragment with Pst I indicated the right orientation of the insert for further manipulations. DNA from one such clone was further restricted with SalI, the 5' overhangs filled-in with the Klenow fragment of DNA polymerase I, then cut with Sac I. The insert fragment was gel purified, and cloned between the Sma I and Sac I sites of pBI121 (Clontech) behind the Cauliflower Mosaic Virus 35S promoter. After checking that the sequence of the junction between insert and vector DNA was appropriate, plasmid DNA from a recombinant clone was used to transform A. tumefaciens (GV3101). Kanamycin resistant colonies were then used for in planta transformation of A. thaliana as previously described.

DNA was extracted from kanamycin resistant seedlings and used to PCR-amplify selected fragments from the hydroxylase using nested primers. When fragments of the expected size could be amplified, corresponding plants were grown in the greenhouse or on agar plates, and fatty acids extracted from fully expanded leaves, roots and dry seeds. GC-MS analysis was then performed as previously described to characterize the different fatty acid species and detect accumulation of hydroxy fatty acids in transgenic tissues.

Example 3

Obtaining Other Plant Fatty Acyl Hydroxylases

In a previous patent application, we described the ways in which the castor fah12 sequence could be used to identify other kappa hydroxylases by methods such as PCR and heterologous hybridization. However, because of the high degree of sequence similarity between Δ12 desaturases and kappa hydroxylases, prior art does not teach how to distinguish between the two kinds of enzymes without a functional test such as demonstrating activity in transgenic plants or another suitable host (e.g., transgenic microbial or animal cells). The identification of the L. fendleri hydroxylase provided for the development of criteria by which a hydroxylase and a desaturase may be distinguished solely on the basis of deduced amino acid sequence information.

FIGS. 9A–B show a sequence alignment of the castor and L. fendleri hydroxylase sequences with the castor hydroxylase sequence and all publically available sequences for all plant microsomal Δ12 fatty acid desaturases. Of the 384 amino acid residues in the castor hydroxylase sequence, more than 95% are identical to the corresponding residue in at least one of the desaturase sequences. Therefore, none of these residues are responsible for the catalytic differences between the hydroxylase and the desaturases. Of the remaining 16 residues in the castor hydroxylase and 14 residues in the Lesquerella hydroxylase, all but six represent instances where the hydroxylase sequence has a conservative substitution compared with one or more of the desaturase sequences, or there is wide variability in the amino acid at that position in the various desaturases. By conservative, we mean that the following amino acids are functionally equivalent : Ser/Thr, Ile/ Leu/ Val/ Met, Asp/ Glu. Thus, these structural differences also cannot account for the catalytic differences between the desaturases and hydroxylases. This leaves just six amino acid residues where both the castor hydroxylase and the Lesquerella hydroxylase differ from all of the known desaturases and where all of the known microsomal Δ12 desaturases have the identical amino acid residue. These residues occur at positions 69, 111, 155, 226, 304 and 331 of the alignment in FIG. 9. Therefore, these six sites distinguish hydroxylases from desaturases. Based on this analysis, we claim that any enzyme with greater than 60% sequence identity to one of the enzymes listed in FIG. 9 can be classified as a hydroxylase if it differs from the sequence of the desaturases at these six positions. Because of slight differences in the number of residues in a particular protein, the numbering may vary from protein to protein but the intent of the number system will be evident if the protein in question is aligned with the castor hydroxylase using the numbering system shown herein. Thus, in conjunction with the methods for using the lesquerella hydroxylase gene to isolate homologous genes, the structural criterion disclosed here teaches how to isolate and identify plant kappa hydroxylase genes for the purpose of genetically modifying fatty acid composition as disclosed herein and in the previous application (No. 08/320,982).

In considering which of the six substitutions are solely or primarily responsible for the difference in catalytic activity of the hydroxylases of this invention and the desaturases, we consider it likely that the substitution of a Phe for a Tyr at position 226 may be solely responsible for this difference in catalytic activity because of the known participation of tyrosine radicals in enzyme catalysis. Other substitutions, such as the Ala for Ser at position 331 may have effects at modulating the overall rate of the reaction. On this basis we envision creating novel kappa hydroxylases by site directed mutagenesis of Δ12 desaturases. We also envision converting Δ15 desaturases and Δ9 desaturases to hydroxylases by similar use of site-directed mutagenesis.

Concluding Remarks

By the above examples, demonstration of critical factors in the production of novel hydroxylated fatty acids by expression of a kappa hydroxylase gene from Castor in transgenic plants is described. In addition, a complete CDNA sequence of the Lesquerella fendleri kappa hydroxylase is also provided. A full sequence of the castor hydroxylase is also given with various constructs for use in host cells. Through this invention, one can obtain the amino acid and nucleic acid sequences which encode plant fatty acyl hydroxylases from a variety of sources and for a variety of applications.

All publications mentioned in this specification are indicative of the level of skill of those skilled in the art to which this invention pertains. All publications are herein incorporated by reference to the same extent as if each individual publication was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

References

Atsmon, D. (1989) Castor, in *Oil Crops of the World*, Robbelen, G., Downey, K. R., and Ashri, A., Eds., McGraw-Hill, New York, pp. 438–447.

Bechtold, N., Ellis, J. and Pelletier, G. (1993) In Planta Agrobacterium mediated gene transfer by infiltration of adult *Arabidopsis thaliana* plants. C. R. Acad. Sci. Paris 316, 1194–1199.

Beltz, G. A., Jacobs, K. A., Eickbuch, T. H., Cherbas, P. T., Kafatos, F. C. (1983) Isolation of multigene families and determination of homologies by filter hybridization methods. Methods in Enzymology 100, 266–285.

Bray, E. A., Naito, S., Pan, N. S., Anderson, E., Dube, P., Beachy, R. N. (1987) Expression of the β-subunit of β-conglycinin in seeds of transgenic plants. Planta 172:364–370.

Carlson, K. D., Chaudhry, A., Bagby, M. O (1990) Analysis of oil and meal from *Lesquerella fendleri* seed. J. Am. Oil Chem. Soc. 67, 438–442.

Ditta, G., Stanfield, S., Corbin, D., Helinski, D. R. (1980) Broad host range DNA cloning system for gram-negative bacteria: Construction of a gene bank of *Rhizobium meliloti*. Proc. Natl. Acad. Sci. USA 77,7347–7351.

Gould, S. J., Subramani, S., Scheffler, I. E. (1989) Use of the DNA polymerase chain reaction for homology probing. Proc. Natl. Acad. Sci. USA 86, 1934–1938.

Hirsinger, F. (1989) New oil crops, in *Oil Crops of the World*, Robbelen, G., Downey, K. R., and Ashri, A., Eds., McGraw-Hill, New York, pp. 518–533.

Howling, D., Morris, L. J., Gurr, M. I., James, A. T. (1972) The specificity of fatty acid desaturases and hydroxylases. The dehydrogenation and hydroxylation of monoenoic acids, Biochim. Biophys. Acta 260, 10.

Huyuh, T. V., Young, R. A., Davis, R. W. (1985) Constructing and screening cDNA libraries in λgtio and λgtll. In DNA Cloning, Vol. 1: A Practical Approach, (ed) D. M. Glover. IRL Press, Washington DC pp 49–77.

Iba, K., Gibson, S., Nishiuchi, T., Fuse, T., Nishimura, M., Arondel, V., Hugly, S., and Somerville, C. (1993) A gene encoding a chloroplast omega-3 fatty acid desaturase complements alterations in fatty acid desaturation and chloroplast copy number of the fad7 mutant of *Arabidopsis thaliana*. J. Biol. Chem. 268, 24099–24105.

Jones, J. D. G., Shlumukov, L., Carland, F., English, J., Scofield, S., Bishop, G. J., Harrison, K. (1992) Effective vectors for transformation, expression of heterologous genes, and assaying transposon excision in transgenic plants. Transgenic Res. 1,285–297.

Knutson, D. S., Thompson, G. A., Radke, S. E., Johnson, W. B., Knauf, V. C., Kridl, J. C. (1992) Proc. Natl. Acad. Sci. USA 89, 2624–2628.

Koncz, C., Schell, J. (1986) The promoter of $T_L$-DNA gene 5 controls the tissue-specific expression of chimeric genes carried by a novel type of Agrobacterium binary vector. Mol. Gen. Genet. 204, 383–396.

Miquel, M. Browse, J. (1992) Arabidopsis mutants deficient in polyunsaturated fatty acid synthesis. J. Biol. Chem. 267, 1502–1509.

Murray, M. G., Thompson, W. F. (1980) Rapid isolation of high molecular weight plant DNA. Nucl. Acid Res. 8,4321–4325.

Okuley, J., Lightner, J., Feldman, K., Yadav, N., Lark, E., Browse, J. (1994) Arabidopsis FAD2 gene encodes the enzyme that is essential for polyunsaturated lipid Sambrook, J., Fritsch, E. F., and Maniatis, T., *Molecular Cloning: a Laboratory Manual*, 2nd ed., Cold Spring Harbor Laboratory Press, 1989.

Smith C. R., Jr. (1985) Unusual seed oils and their fatty acids, in *Fatty Acids*, Pryde E. H., Ed., American Oil Chemists' Society, Champaign, Second edition, pp 29–47.

van de Loo, F. J., Fox, B. G., Somerville, C. (1993) Unusual fatty acids, in *Lipid Metabolism in Plants*, T. S. Moore Jr., Ed., CRC Press, Boca Raton, pp91–126.

van de Loo, F. N., Turner, S., Somerville, C. R. (1995) An oleate 12-hydroxylase from castor (*Ricinus communes* L.) is a fatty acyl desaturase homolog. Proc. Natl. Acad. Sci. USA 92,6743–6747 von Heijne, G. (1985) Signal sequences. J. Mol. Biol. 184,99–105

What is claimed is:

1. A method of increasing the amount of a hydroxylated fatty acyl compound in a seed of a plant from a given percentage of hydroxylated fatty acyl compound to an increased percentage of hydroxylated fatty acyl compound comprising; growing a plant producing said seed having integrated in its genome a DNA construct, said DNA construct comprising in the 5' to 3' direction of transcription, a transcriptional regulatory region functional in said plant and a region encoding kappa hydroxylase, under conditions which will permit the transcription and translation of said kappa hydroxylase region, whereby said increased percentage of hydroxylated fatty acyl compound is produced in said seed, wherein said kappa hydroxylase region encodes amino acid sequence SEQ ID NO:4.

2. The method of claim 1 wherein said kappa hydroxylase region comprises base 402 to base 1553 of SEQ ID NO:3.

3. The method of claim 1 wherein said plant is selected from the group consisting of Brassica, Canola, coconut, corn, cotton, Crambe, Cuphea, flax, oil palm, peanut, rapeseed, safflower, soybean, and sunflower.

4. The method of claim 1 wherein said hydroxylated fatty acyl compound comprises a hydroxylated fatty acid selected from The group consisting of 12-hydroxy-9-octadecenoic acid (ricinoleic acid) and 14-hydroxy-11-eicosenoic acid (lesquerolic acid).

5. The method of claim 1 further comprising metabolizing said hydroxylated fatty acyl compound with an enzyme.

6. The method of claim 5 wherein said hydroxylated fatty acyl compound comprises 12-hydroxy-9-octadecenoic acid (ricinoleic acid) and said enzyme is a desaturase.

7. A method of producing a hydroxylated fatty acyl compound in a seed of a plant comprising:

(a) providing a fatty acyl compound in said seed of said plant, wherein said fatty acyl compound is a substrate for kappa hydroxylase; and (b) expressing kappa hydroxylase from an integrated DNA construct in said seed of said plant to hydroxylate said fatty acyl compound, wherein said DNA construct comprises a region encoding a kappa hydroxylase, whereby said hydroxylated fatty acyl compound is produced in said seed of said plant, wherein said kappa hydroxylase region encodes amino acid sequence SEQ ID NO:4.

8. The method of claim 7 wherein said kappa hydroxylase region comprises base 402 to base 1553 of SEQ ID NO:3.

9. The method of claim 7 wherein said plant is selected from the group consisting of Brassica, Canola, coconut, corn, cotton, Crambe, Cuphea, flax, oil Palm, peanut, rapeseed, safflower, soybean, and sunflower.

10. The method of claim 7 wherein said fatty acyl compound comprises a fatty acid selected from the group consisting of 9-octadecenoic acid (oleic acid) and 11-eicosenoic acid.

11. The method of claim 7 wherein said hydroxylated fatty acyl compound comprises a hydroxylated fatty acid selected from the group consisting of 12-hydroxy-9-octadecenoic acid (ricinoleic acid) and 14-hydroxy-11-eicosenoic acid (lesquerolic acid).

12. The method of claim 7 wherein said fatty acyl compound is provided by transgenic means.

13. The method of claim 7 further comprising metabolizing said hydroxylated fatty acyl compound with an enzyme.

14. The method of claim 13 wherein said hydroxylated fatty acyl compound comprises 12-hydroxy-9-octadecenoic acid (ricinoleic acid) and said enzyme is a desaturase.

15. A method of producing a hydroxylated fatty acyl compound in a seed of a plant comprising:

(a) providing a fatty acyl compound in said seed of said plant, wherein said fatty acyl compound comprises a fatty acid selected from the group consisting, of hexadecenoic acid octadecenoic acid, eicosenio acid, and docosenoic acid, wherein said fatty acid contains a double bond;

(b) expressing kappa hydroxylase from an integrated DNA construct in said seed of said plant, wherein said DNA construct comprises a region encoding amino acid sequence SEQ ID NO:4; and (c) hydroxylating said fatty acyl compound with said kappa hydroxylase to produce said hydroxylated fatty acyl compound in said seed of said plant.

16. The method of claim 15 wherein said DNA construct comprises base 402 to base 1553 of SEQ ID NO:3.

17. The method of claim 15 wherein said plant is selected from the group consisting of Brassuca, Canola, coconut, corn, cotton, Crambe, Cuphea, flax, oil palm, peanut, rapeseed, safflower, soybean and sunflower.

18. The method of claim 15 wherein said fatty acid is selected from the group consisting of 9-octadecenoic acid (oleic acid) and 11-eicosenoic acid.

19. The method of claim 15 wherein said hydroxylated fatty acyl compound comprises a hydroxylated fatty acid selected from the group consisting of 12-hydroxy-9-octadecenoic acid (ricinoleic acid) and 14-hydroxy-11-eicosenoic acid (lesquerolic acid).

20. The method of claim 15 wherein said fatty acyl compound is provided by transgenic means.

21. The method of claim 15 further comprising metabolizing said hydroxylated fatty acyl compound with an enzyme.

22. The method of claim 21 wherein said hydroxylated fatty acyl compound comprises 12-hydroxy-9-octadecenoic acid (ricinoleic acid) and said enzyme is a desaturase.

* * * * *

SEQUENCE LISTING (1) GENERAL INFORMATION:

(iii) NUMBER OF SEQUENCES:   15

(2) INFORMATION FOR SEQ ID NO:1:

(i) SEQUENCE CHARACTERISTICS:
      (A) LENGTH:              543 nucleotides
      (B) TYPE:                nucleotide
      (C) STRANDEDNESS:        single
      (D) TOPOLOGY:            linear

```
        (ii) MOLECULE TYPE:                  cDNA (xi) SEQUENCE DESCRIPTION: SEQ ID NO:1:

TATTGGCACC GGCGGCACCA TTCCAACAAT GGATCCCTAG AAAAAGATGA AGTCTTTGTC      60

CCACCTAAGA AAGCTGCAGT CANATGGTAT GTCAAATACC TCAACAACCC TCTTGGACGC     120

ATTCTGGTGT TAACAGTTCA GTTTATCCTC GGGTGGCCTT TGTATCTAGC CTTTAATGTA     180

TCAGGTAGAC CTTATGATGG TTTCGCTTCA CATTTCTTCC CTCATGCACC TATCTTTAAG     240

GACCGTGAAC GTCTCCAGAT ATACATCTCA GATGCTGGTA TTCTAGCTGT CTGTTATGGT     300

CTTTACCGTT ACGCTGCTTC ACAAGGATTG ACTGCTATGA TCTGCGTCTA CGGAGTACCG     360

CTTTTGATAG TGAACTTTTT CCTTGTCTTG GTCACTTTCT TGCAGCACAC TCATCCTTCA     420

TTACCTCACT ATGATTCAAC CGAGTGGGAA TGGATTAGAG GAGCTTTGGT TACGGTAGAC     480

AGAGACTATG GAATCTTGAA CAAGGTGTTT CACAACATAA CAGACACCCA CGTAGCACAC     540

CAC                                                                  543

(2) INFORMATION FOR SEQ ID NO:2:

(i) SEQUENCE CHARACTERISTICS:
            (A) LENGTH:             544 nucleotides
            (B) TYPE:                nucleotide
            (C) STRANDEDNESS:        single
            (D) TOPOLOGY:            linear (ii) MOLECULE TYPE:                  cDNA (xi) SEQUENCE DESCRIPTION: SEQ ID NO:2:

TATAGGCACC GGAGGCACCA TTCCAACACA GGATCCCTCG AAAGAGATGA AGTATTTGTC      60

CCAAAGCAGA AATCCGCAAT CAAGTGGTAC GGCGAATACC TCAACAACCC TCCTGGTCGC     120

ATCATGATGT TAACTGTCCA GTTCGTCCTC GGATGGCCCT TGTACTTAGC CTTCAACGTT     180

TCTGGCAGAC CCTACAATGG TTTCGCTTCC CATTTCTTCC CCAATGCTCC TATCTACAAC     240

GACCGTGAAC GCCTCCAGAT TTACATCTCT GATGCTGGTA TTCTAGCCGT CTGTTATGGT     300

CTTTACCGTT ACGCTGTTGC ACAAGGACTA GCCTCAATGA TCTGTCTAAA CGGAGTTCCG     360

CTTCTGATAG TTAACTTTTT CCTCGTCTTG ATCACTTACT TACAACACAC TCACCCTGCG     420

TTGCCTCACT ATGATTCATC AGAGTGGGAT TGGCTTAGAG GAGCTTTAGC TACTGTAGAC     480

AGAGACTATG GAATCTTGAA CAAGGTGTTC CATAACATCA CAGACACCCA CGTCGCACAC     540

CACT                                                                 544

(2) INFORMATION FOR SEQ ID NO:3:

(i) SEQUENCE CHARACTERISTICS:
            (A) LENGTH:             1855 nucleotides
            (B) TYPE:                nucleotide
            (C) STRANDEDNESS:        single
            (D) TOPOLOGY:            linear (ii) MOLECULE TYPE:                  genomic (xi) SEQUENCE DESCRIPTION: SEQ ID NO:3:

ATGAAGCTTT ATAAGAAGTT AGTTTTCTCT GGTGACAGAG AAATTNTGTC AATTGGTAGT      60

GACAGTTGAA GCAACAGGAA CAACAAGGAT GGTTGGTGNT GATGCTGATG TGGTGATGTG     120

TTATTCATCA AATACTAAAT ACTACATTAC TTGTTGCTGC CTACTTCTCC TATTTCCTCC     180

GCCACCCATT TTGGACCCAC GANCCTTCCA TTTAAACCCT CTCTCGTGCT ATTCACCAGA     240

AGAGAAGCCA AGAGAGAGAG AGAGAGAATG TTCTGAGGAT CATTGTCTTC TTCATCGTTA     300
```

-continued

```
TTAACGTAAG TTTTTTTTGA CCACTCATAT CTAAAATCTA GTACATGCAA TAGATTAATG    360
ACTGTTCCTT CTTTTGATAT TTTCAGCTTC TTGAATTCAA GATGGGTGCT GGTGGAAGAA    420
TAATGGTTAC CCCCTCTTCC AAGAAATCAG AAACTGAAGC CCTAAAACGT GGACCATGTG    480
AGAAACCACC ATTCACTGTT AAAGATCTGA AGAAAGCAAT CCCACAGCAT TGTTTCAAGC    540
GCTCTATCCC TCGTTCTTTC TCCTACCTTC TCACAGATAT CACTTTAGTT TCTTGCTTCT    600
ACTACGTTGC CACAAATTAC TTCTCTCTTC TTCCTCAGCC TCTCTCTACT TACCTAGCTT    660
GGCCTCTCTA TTGGGTATGT CAAGGCTGTG TCTTAACCGG TATCTGGGTC ATTGGCCATG    720
AATGTGGTCA CCATGCATTC AGTGACTATC AATGGGTAGA TGACACTGTT GGTTTTATCT    780
TCCATTCCTT CCTTCTCGTC CCTTACTTCT CCTGGAAATA CAGTCATCGT CGTCACCATT    840
CCAACAATGG ATCTCTCGAG AAAGATGAAG TCTTTGTCCC ACCGAAGAAA GCTGCAGTCA    900
AATGGTATGT TAAATACCTC AACAACCCTC TTGGACGCAT TCTGGTGTTA ACAGTTCAGT    960
TTATCCTCGG GTGGCCTTTG TATCTAGCCT TTAATGTATC AGGTAGACCT TATGATGGTT   1020
TCGCTTCACA TTTCTTCCCT CATGCACCTA TCTTTAAAGA CCGAGAACGC CTCCAGATAT   1080
ACATCTCAGA TGCTGGTATT CTAGCTGTCT GTTATGGTCT TACCGTTAC GCTGCTTCAC    1140
AAGGATTGAC TGCTATGATC TGCGTCTATG AGTACCGCT TTTGATAGTG AACTTTTTCC    1200
TTGTCTTGGT AACTTTCTTG CAGCACACTC ATCCTTCGTT ACCTCATTAT GATTCAACCG   1260
AGTGGGAATG GATTAGAGGA GCTTTGGTTA CGGTAGACAG AGACTATGGA ATATTGAACA   1320
AGGTGTTCCA TAACATAACA GACACACATG TGGCTCATCA TCTCTTTGCA ACTATACCGC   1380
ATTATAACGC AATGGAAGCT ACAGAGGCGA TAAAGCCAAT ACTTGGTGAT TACTACCACT   1440
TCGATGGAAC ACCGTGGTAT GTGGCCATGT ATAGGGAAGC AAAGGAGTGT CTCTATGTAG   1500
AACCGGATAC GGAACGTGGG AAGAAAGGTG TCTACTATTA CAACAATAAG TTATGAGGCT   1560
GATAGGGCGA GAGAAGTGCA ATTATCAATC TTCATTTCCA TGTTTTAGGT GTCTTGTTTA   1620
AGAAGCTATG CTTTGTTTCA ATAATCTCAG AGTCCATNTA GTTGTGTTCT GGTGCATTTT   1680
GCCTAGTTAT GTGGTGTCGG AAGTTAGTGT TCAAACTGCT TCCTGCTGTG CTGCCCAGTG   1740
AAGAACAAGT TTACGTGTTT AAAATACTCG GAACGAATTG ACCACAANAT ATCCAAAACC   1800
GGCTATCCGA ATTCCATATC CGAAAACCGG ATATCCAAAT TTCCAGAGTA CTTAG         1855
```

(2) INFORMATION FOR SEQ ID NO:4:

(i) SEQUENCE CHARACTERISTICS:
        (A) LENGTH: 384 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:4:

```
Met Gly Ala Gly Gly Arg Ile Met Val Thr Pro Ser Ser Lys Lys Ser
                                  10

Glu Thr Glu Ala Leu Lys Arg Gly Pro Cys Glu Lys Pro Pro Phe Thr
                 20                                  30

Val Lys Asp Leu Lys Lys Ala Ile Pro Gln His Cys Phe Lys Arg Ser
                                  40

Ile Pro Arg Ser Phe Ser Tyr Leu Leu Thr Asp Ile Thr Leu Val Ser
    50                                              60

Cys Phe Tyr Tyr Val Ala Thr Asn Tyr Phe Ser Leu Leu Pro Gln Pro
                 70                                  80
```

```
Leu Ser Thr Tyr Leu Ala Trp Pro Leu Tyr Trp Val Cys Gln Gly Cys
                             90

Val Leu Thr Gly Ile Trp Val Ile Gly His Glu Cys Gly His His Ala
            100                                 110

Phe Ser Asp Tyr Gln Trp Val Asp Asp Thr Val Gly Phe Ile Phe His
                            120

Ser Phe Leu Leu Val Pro Tyr Phe Ser Trp Lys Tyr Ser His Arg Arg
            130                                 140

His His Ser Asn Asn Gly Ser Leu Glu Lys Asp Glu Val Phe Val Pro
                            150                                 160

Pro Lys Lys Ala Ala Val Lys Trp Tyr Val Lys Tyr Leu Asn Asn Pro
                            170

Leu Gly Arg Ile Leu Val Leu Thr Val Gln Phe Ile Leu Gly Trp Pro
            180                                 190

Leu Tyr Leu Ala Phe Asn Val Ser Gly Arg Pro Tyr Asp Gly Phe Ala
                            200

Ser His Phe Phe Pro His Ala Pro Ile Phe Lys Asp Arg Glu Arg Leu
            210                                 220

Gln Ile Tyr Ile Ser Asp Ala Gly Ile Leu Ala Val Cys Tyr Gly Leu
                            230                                 240

Tyr Arg Tyr Ala Ala Ser Gln Gly Leu Thr Ala Met Ile Cys Val Tyr
                            250

Gly Val Pro Leu Leu Ile Val Asn Phe Phe Leu Val Leu Val Thr Phe
            260                                 270

Leu Gln His Thr His Pro Ser Leu Pro His Tyr Asp Ser Thr Glu Trp
                            280

Glu Trp Ile Arg Gly Ala Leu Val Thr Val Asp Arg Asp Tyr Gly Ile
            290                                 300

Leu Asn Lys Val Phe His Asn Ile Thr Asp Thr His Val Ala His His
                            310                                 320

Leu Phe Ala Thr Ile Pro His Tyr Asn Ala Met Glu Ala Thr Glu Ala
                            330

Ile Lys Pro Ile Leu Gly Asp Tyr Tyr His Phe Asp Gly Thr Pro Trp
            340                                 350

Tyr Val Ala Met Tyr Arg Glu Ala Lys Glu Cys Leu Tyr Val Glu Pro
                            360

Asp Thr Glu Arg Gly Lys Lys Gly Val Tyr Tyr Asn Asn Lys Leu
            370                                 380

(2) INFORMATION FOR SEQ ID NO:5:

(i) SEQUENCE CHARACTERISTICS:
        (A) LENGTH:              387 amino acids
        (B) TYPE:                amino acid
        (C) STRANDEDNESS:
        (D) TOPOLOGY:            linear (ii) MOLECULE TYPE:                  protein (xi) SEQUENCE DESCRIPTION: SEQ ID NO:5:

Met Gly Gly Gly Gly Arg Met Ser Thr Val Ile Thr Ser Asn Asn Ser
                             10

Glu Lys Lys Gly Gly Ser Ser His Leu Lys Arg Ala Pro His Thr Lys
             20                                 30

Pro Pro Phe Thr Leu Gly Asp Leu Lys Arg Ala Ile Pro Pro His Cys
                             40
```

```
Phe Glu Arg Ser Phe Val Arg Ser Phe Ser Tyr Val Ala Tyr Asp Val
 50                                  60
Cys Leu Ser Phe Leu Phe Tyr Ser Ile Ala Thr Asn Phe Pro Tyr
                     70                                      80
Ile Ser Ser Pro Leu Ser Tyr Val Ala Trp Leu Val Tyr Trp Leu Phe
                                  90
Gln Gly Cys Ile Leu Thr Gly Leu Trp Val Ile Gly His Glu Cys Gly
            100                                 110
His His Ala Phe Ser Glu Tyr Gln Leu Ala Asp Ile Val Gly Leu
                         120
Ile Val His Ser Ala Leu Leu Val Pro Tyr Phe Ser Trp Lys Tyr Ser
    130                                 140
His Arg Arg His His Ser Asn Ile Gly Ser Leu Glu Arg Asp Glu Val
                 150                                         160
Phe Val Pro Lys Ser Lys Ser Lys Ile Ser Trp Tyr Ser Lys Tyr Ser
                                 170
Asn Asn Pro Pro Gly Arg Val Leu Thr Leu Ala Ala Thr Leu Leu Leu
            180                                 190
Gly Trp Pro Leu Tyr Leu Ala Phe Asn Val Ser Gly Arg Pro Tyr Asp
                             200
Arg Phe Ala Cys His Tyr Asp Pro Tyr Gly Pro Ile Phe Ser Glu Arg
    210                                     220
Glu Arg Leu Gln Ile Tyr Ile Ala Asp Leu Gly Ile Phe Ala Thr Thr
                     230                                     240
Phe Val Leu Tyr Gln Ala Thr Met Ala Lys Gly Leu Ala Trp Val Met
                             250
Arg Ile Tyr Gly Val Pro Leu Leu Ile Val Asn Cys Phe Leu Val Met
                260                                     270
Ile Thr Tyr Leu Gln His Thr His Pro Ala Ile Pro Arg Tyr Gly Ser
                         280
Ser Glu Trp Asp Trp Leu Arg Gly Ala Met Val Thr Val Asp Arg Asp
    290                                         300
Tyr Gly Val Leu Asn Lys Val Phe His Asn Ile Ala Asp Thr His Val
                     310                                     320
Ala His His Leu Phe Ala Thr Val Pro His Tyr His Ala Met Glu Ala
                             330
Thr Lys Ala Ile Lys Pro Ile Met Gly Glu Tyr Tyr Arg Tyr Asp Gly
            340                                     350
Thr Pro Phe Tyr Lys Ala Leu Trp Arg Glu Ala Lys Glu Cys Leu Phe
                             360
Val Glu Pro Asp Glu Gly Ala Pro Thr Gln Gly Val Phe Trp Tyr Arg
    370                                         380
Asn Lys Tyr (2) INFORMATION FOR SEQ ID NO:6:

(i) SEQUENCE CHARACTERISTICS:
        (A) LENGTH:             383 amino acids
        (B) TYPE:               amino acid
        (C) STRANDEDNESS:
        (D) TOPOLOGY:           linear (ii) MOLECULE TYPE:                 protein
```

(xi) SEQUENCE DESCRIPTION: SEQ ID NO:6:

Met Gly Ala Gly Gly Arg Met Pro Val Pro Thr Ser Ser Lys Lys Ser
                                  10

Glu Thr Asp Thr Thr Lys Arg Val Pro Cys Glu Lys Pro Pro Phe Ser
            20                                  30

Val Gly Asp Leu Lys Lys Ala Ile Pro Pro His Cys Phe Lys Arg Ser
                        40

Ile Pro Arg Ser Phe Ser Tyr Leu Ile Ser Asp Ile Ile Ala Ser
        50                                  60

Cys Phe Tyr Tyr Val Ala Thr Asn Tyr Phe Ser Leu Leu Pro Gln Pro
                    70                                  80

Leu Ser Tyr Leu Ala Trp Pro Leu Tyr Trp Ala Cys Gln Gly Cys Val
                                90

Leu Thr Gly Ile Trp Val Ile Ala His Glu Cys Gly His His Ala Phe
                100                                 110

Ser Asp Tyr Gln Trp Leu Asp Asp Thr Val Gly Leu Ile Phe His Ser
                            120

Phe Leu Leu Val Pro Tyr Phe Ser Trp Lys Tyr Ser His Arg Arg His
        130                                 140

His Ser Asn Thr Gly Ser Leu Glu Arg Asp Glu Val Phe Val Pro Lys
                        150                                 160

Gln Lys Ser Ala Ile Lys Trp Tyr Gly Lys Tyr Leu Asn Asn Pro Leu
                                170

Gly Arg Ile Met Met Leu Thr Val Gln Phe Val Leu Gly Trp Pro Leu
                180                                 190

Tyr Leu Ala Phe Asn Val Ser Gly Arg Pro Tyr Asp Gly Phe Ala Cys
                            200

His Phe Phe Pro Asn Ala Pro Ile Tyr Asn Asp Arg Glu Arg Leu Gln
        210                                 220

Ile Tyr Leu Ser Asp Ala Gly Ile Leu Ala Val Cys Phe Gly Leu Tyr
                        230                                 240

Arg Tyr Ala Ala Ala Gln Gly Met Ala Ser Met Ile Cys Leu Tyr Gly
                                250

Val Pro Leu Leu Ile Val Asn Ala Phe Leu Val Leu Ile Thr Tyr Leu
                260                                 270

Gln His Thr His Pro Ser Leu Pro His Tyr Asp Ser Ser Glu Trp Asp
                            280

Trp Leu Arg Gly Ala Leu Ala Thr Val Asp Arg Asp Tyr Gly Ile Leu
        290                                 300

Asn Lys Val Phe His Asn Ile Thr Asp Thr His Val Ala His His Leu
                        310                                 320

Phe Ser Thr Met Pro His Tyr Asn Ala Met Glu Ala Thr Lys Ala Ile
                                330

Lys Pro Ile Leu Gly Asp Tyr Tyr Gln Phe Asp Gly Thr Pro Trp Tyr
                340                                 350

Val Ala Met Tyr Arg Glu Ala Lys Glu Cys Ile Tyr Val Glu Pro Asp
                            360

Arg Glu Gly Asp Lys Lys Gly Val Tyr Trp Tyr Asn Asn Lys Leu
        370                                 380

(2) INFORMATION FOR SEQ ID NO:7:

(i) SEQUENCE CHARACTERISTICS:
        (A) LENGTH:                 384 amino acids
        (B) TYPE:                   amino acid
        (C) STRANDEDNESS:
        (D) TOPOLOGY:              linear (ii) MOLECULE TYPE:           protein (xi) SEQUENCE DESCRIPTION: SEQ ID NO:7:

```
Met Gly Ala Gly Gly Arg Met Gln Val Ser Pro Ser Lys Lys Ser
                                 10

Glu Thr Asp Asn Ile Lys Arg Val Pro Cys Glu Thr Pro Phe Thr
             20                              30

Val Gly Glu Leu Lys Lys Ala Ile Pro Pro His Cys Phe Lys Arg Ser
                         40

Ile Pro Arg Ser Phe Ser His Leu Ile Trp Asp Ile Ile Ala Ser
     50                                  60

Cys Phe Tyr Tyr Val Ala Thr Thr Tyr Phe Pro Leu Leu Pro Asn Pro
                     70                                      80

Leu Ser Tyr Phe Ala Trp Pro Leu Tyr Trp Ala Cys Gln Gly Cys Val
                             90

Leu Thr Gly Val Trp Val Ile Ala His Glu Cys Gly His Ala Ala Phe
                100                                    110

Ser Asp Tyr Gln Trp Leu Asp Asp Thr Val Gly Leu Ile Phe His Ser
                         120

Phe Leu Leu Val Pro Tyr Phe Ser Trp Lys Tyr Ser His Arg Arg His
     130                                 140

His Ser Asn Thr Gly Ser Leu Glu Arg Asp Glu Val Phe Val Pro Arg
                    150                                     160

Arg Ser Gln Thr Ser Ser Gly Thr Ala Ser Thr Ser Thr Thr Phe Gly
                                 170

Arg Thr Val Met Leu Thr Val Gln Phe Thr Leu Gly Trp Pro Leu Tyr
                180                                 190

Leu Ala Phe Asn Val Ser Gly Arg Pro Tyr Asp Gly Gly Phe Ala Cys
                             200

His Phe His Pro Asn Ala Pro Ile Tyr Asn Asp Arg Glu Arg Leu Gln
     210                                 220

Ile Tyr Ile Ser Asp Ala Gly Ile Leu Ala Val Cys Tyr Gly Leu Leu
                    230                                     240

Pro Tyr Ala Ala Val Gln Gly Val Ala Ser Met Val Cys Phe Leu Arg
                                 250

Val Pro Leu Leu Ile Val Asn Gly Phe Leu Val Leu Ile Thr Tyr Leu
                260                                 270

Gln His Thr His Pro Ser Leu Pro His Tyr Asp Ser Ser Glu Trp Asp
                             280

Trp Leu Arg Gly Ala Leu Ala Thr Val Asp Arg Asp Tyr Gly Ile Leu
     290                                 300

Asn Gln Gly Phe His Asn Ile Thr Asp Thr His Glu Ala His His Leu
                    310                                     320

Phe Ser Thr Met Pro His Tyr His Ala Met Glu Ala Thr Lys Ala Ile
                                 330

Lys Pro Ile Leu Gly Glu Tyr Tyr Gln Phe Asp Gly Thr Pro Val Val
                340                                 350
```

```
Lys Ala Met Trp Arg Glu Ala Lys Glu Cys Ile Tyr Val Glu Pro Asp
                            360

Arg Gln Gly Glu Lys Lys Gly Val Phe Trp Tyr Asn Asn Lys Leu Xaa
        370                                 380
```

(2) INFORMATION FOR SEQ ID NO:8:

(i) SEQUENCE CHARACTERISTICS:
        (A) LENGTH:               309 amino acids
        (B) TYPE:                 amino acid
        (C) STRANDEDNESS:
        (D) TOPOLOGY:           linear (ii) MOLECULE TYPE:           protein (xi) SEQUENCE DESCRIPTION: SEQ ID NO:8:

```
Ser Leu Leu Thr Ser Phe Ser Tyr Val Val Tyr Asp Leu Ser Phe Ala
                            10

Phe Ile Phe Tyr Ile Ala Thr Thr Tyr Phe His Leu Leu Pro Gln Pro
        20                                  30

Phe Ser Leu Ile Ala Trp Pro Ile Tyr Trp Val Leu Gln Gly Cys Leu
                    40

Leu Thr Arg Val Cys Gly His His Ala Phe Ser Lys Tyr Gln Trp Val
    50                                  60

Asp Val Val Gly Leu Thr Leu His Ser Thr Leu Leu Val Pro Tyr
                70                                          80

Phe Ser Trp Lys Ile Ser His Arg Arg His His Ser Asn Thr Gly Ser
                            90

Leu Asp Arg Asp Glu Arg Val Lys Val Ala Trp Phe Ser Lys Tyr Leu
        100                                 110

Asn Asn Pro Leu Gly Arg Ala Val Ser Leu Leu Val Thr Leu Thr Ile
                    120

Gly Trp Pro Met Tyr Leu Ala Phe Asn Val Ser Gly Arg Pro Tyr Asp
    130                                 140

Ser Phe Ala Ser His Tyr His Pro Tyr Arg Val Arg Leu Leu Ile Tyr
                150                                 160

Val Ser Asp Val Ala Leu Phe Ser Val Thr Tyr Ser Leu Tyr Arg Val
                            170

Ala Thr Leu Lys Gly Leu Val Trp Leu Leu Cys Val Tyr Gly Val Pro
        180                                 190

Leu Leu Ile Val Asn Gly Phe Leu Val Thr Ile Thr Tyr Leu Arg Val
                    200

His Tyr Asp Ser Ser Glu Trp Asp Trp Leu Lys Gly Ala Leu Ala Thr
    210                                 220

Met Asp Arg Asp Tyr Gly Ile Leu Asn Lys Val Phe His His Ile Thr
                230                                 240

Asp Thr His Val Ala His His Leu Phe Ser Thr Met Pro His Tyr His
                            250

Leu Arg Val Lys Pro Ile Leu Gly Glu Tyr Tyr Gln Phe Asp Asp Thr
        260                                 270

Pro Phe Tyr Lys Ala Leu Trp Arg Glu Ala Arg Glu Cys Leu Tyr Val
                    280

Glu Pro Asp Glu Gly Thr Ser Glu Lys Gly Val Tyr Trp Tyr Arg Asn
    290                                 300

Lys Tyr Leu Arg Val
```

(2) INFORMATION FOR SEQ ID NO:9:

(i) SEQUENCE CHARACTERISTICS:
        (A) LENGTH:                302 amino acids
        (B) TYPE:                  amino acid
        (C) STRANDEDNESS:
        (D) TOPOLOGY:              linear (ii) MOLECULE TYPE:           protein (xi) SEQUENCE DESCRIPTION: SEQ ID NO:9:

```
Phe Ser Tyr Val Val Tyr Asp Leu Thr Ile Ala Phe Cys Leu Tyr Tyr
                                 10

Val Ala Thr His Tyr Phe His Leu Leu Pro Gly Pro Leu Ser Phe Arg
                20                                  30

Gly Met Ala Ile Tyr Trp Ala Val Gln Gly Cys Ile Leu Thr Gly Val
                            40

Trp Val Val Ala Phe Ser Asp Tyr Gln Leu Leu Asp Asp Ile Val Gly
 50                                              60

Leu Ile Leu His Ser Ala Leu Leu Val Pro Tyr Phe Ser Trp Lys Tyr
                    70                                          80

Ser His Arg Arg His His Ser Asn Thr Gly Ser Leu Glu Arg Asp Glu
                                 90

Val Phe Val Pro Lys Val Ser Lys Tyr Leu Asn Asn Pro Pro Gly Arg
                100                                 110

Val Leu Thr Leu Ala Val Thr Leu Thr Leu Gly Trp Pro Leu Tyr Leu
                            120

Ala Leu Asn Val Ser Gly Arg Pro Tyr Asp Arg Phe Ala Cys His Tyr
130                                              140

Asp Pro Tyr Gly Pro Ile Tyr Ser Val Ile Ser Asp Ala Gly Val Leu
                    150                                         160

Ala Val Val Tyr Gly Leu Phe Arg Leu Ala Met Ala Lys Gly Leu Ala
                                 170

Trp Val Val Cys Val Tyr Gly Val Pro Leu Leu Val Val Asn Gly Phe
                180                                 190

Leu Val Leu Ile Thr Phe Leu Gln His Thr His Val Ser Glu Trp Asp
                            200

Trp Leu Arg Gly Ala Leu Ala Thr Val Asp Arg Asp Tyr Gly Ile Leu
210                                              220

Asn Lys Val Phe His Asn Ile Thr Asp Thr His Val Ala His His Leu
                    230                                         240

Phe Ser Thr Met Pro His Tyr His Ala Met Glu Ala Thr Val Glu Tyr
                                 250

Tyr Arg Phe Asp Glu Thr Pro Phe Val Lys Ala Met Trp Arg Glu Ala
                260                                 270

Arg Glu Cys Ile Tyr Val Glu Pro Asp Gln Ser Thr Glu Ser Lys Gly
                            280

Val Phe Trp Tyr Asn Asn Lys Leu Ala Met Glu Ala Thr Val
    290                                 300
```

(2) INFORMATION FOR SEQ ID NO:10:

(i) SEQUENCE CHARACTERISTICS:
        (A) LENGTH:                372 amino acids
        (B) TYPE:                  amino acid
        (C) STRANDEDNESS:
        (D) TOPOLOGY:              linear (ii) MOLECULE TYPE:           protein -continued (xi) SEQUENCE DESCRIPTION: SEQ ID NO:10:

Met Gly Ala Gly Gly Arg Met Thr Glu Lys Glu Arg Glu Lys Gln Glu
                                10

Gln Leu Ala Arg Ala Thr Gly Gly Ala Ala Met Gln Arg Ser Pro Val
              20                                  30

Glu Lys Pro Pro Phe Thr Leu Gly Gln Ile Lys Lys Ala Ile Pro Pro
                      40

His Cys Phe Glu Arg Ser Val Leu Lys Ser Ser Tyr Val Val His
      50                                          60

Asp Leu Val Ile Ala Ala Leu Leu Tyr Phe Ala Leu Ala Ile Ile
                      70                                      80

Pro Ala Leu Pro Ser Pro Leu Arg Tyr Ala Ala Trp Pro Leu Tyr Trp
                              90

Ile Ala Gln Gly Ala Phe Ser Asp Tyr Ser Leu Leu Asp Asp Val Val
              100                                 110

Gly Leu Val Leu His Ser Ser Leu Met Val Pro Tyr Phe Ser Trp Lys
                      120

Tyr Ser His Arg Arg His His Ser Asn Thr Gly Ser Leu Glu Arg Asp
    130                                 140

Glu Val Phe Val Pro Lys Lys Lys Glu Ala Leu Pro Trp Tyr Thr Pro
                      150                                 160

Tyr Val Tyr Asn Asn Pro Val Gly Arg Val Val His Ile Val Val Gln
                              170

Leu Thr Leu Gly Trp Pro Leu Tyr Leu Ala Thr Asn Ala Ser Gly Arg
              180                                 190

Pro Tyr Pro Arg Phe Ala Cys His Phe Asp Pro Tyr Gly Pro Ile Tyr
                              200

Asn Asp Arg Glu Arg Ala Gln Ile Phe Val Ser Asp Ala Gly Val Val
    210                                 220

Ala Val Ala Phe Gly Leu Tyr Lys Leu Ala Ala Phe Gly Val Trp
              230                                 240

Trp Val Val Arg Val Tyr Ala Val Pro Leu Leu Ile Val Asn Ala Trp
                              250

Leu Val Leu Ile Thr Tyr Leu Gln His Thr His Pro Ser Leu Pro His
              260                                 270

Tyr Asp Ser Ser Glu Trp Asp Trp Leu Arg Gly Ala Leu Ala Thr Met
                      280

Asp Arg Asp Tyr Gly Ile Leu Asn Arg Val Phe His Asn Ile Thr Asp
    290                                 300

Thr His Val Ala His His Leu Phe Ser Thr Met Pro His Tyr His Ala
              310                                 320

Met Glu Ala Thr Lys Ala Ile Arg Pro Ile Leu Gly Asp Tyr Tyr His
                      330

Phe Asp Pro Thr Pro Val Ala Lys Ala Thr Trp Arg Glu Ala Gly Glu
              340                                 350

Cys Ile Tyr Val Glu Pro Glu Asp Arg Lys Gly Val Phe Trp Tyr Asn
                      360

Lys Lys Phe Xaa
    370

(2) INFORMATION FOR SEQ ID NO:11:

(i) SEQUENCE CHARACTERISTICS:
        (A) LENGTH:                    224 amino acids
        (B) TYPE:                      amino acid
        (C) STRANDEDNESS:
        (D) TOPOLOGY:                linear (ii) MOLECULE TYPE:           protein (xi) SEQUENCE DESCRIPTION: SEQ ID NO:11:

```
Trp Val Met Ala His Asp Cys Gly His His Ala Phe Ser Asp Tyr Gln
                             10
Leu Leu Asp Asp Val Val Gly Leu Ile Leu His Ser Cys Leu Leu Val
             20                              30
Pro Tyr Phe Ser Trp Lys His Ser His Arg Arg His His Ser Asn Thr
                     40
Gly Ser Leu Glu Arg Asp Glu Val Phe Val Pro Lys Lys Lys Ser Ser
     50                              60
Ile Arg Trp Tyr Ser Lys Tyr Leu Asn Asn Pro Pro Gly Arg Ile Met
                 70                                          80
Thr Ile Ala Val Thr Leu Ser Leu Gly Trp Pro Leu Tyr Leu Ala Phe
                             90
Asn Val Ser Gly Arg Pro Tyr Asp Arg Phe Ala Cys His Tyr Asp Pro
            100                             110
Tyr Gly Pro Ile Tyr Asn Asp Arg Glu Arg Ile Glu Ile Phe Ile Ser
                    120
Asp Ala Gly Val Leu Ala Val Thr Phe Gly Leu Tyr Gln Leu Ala Ile
    130                             140
Ala Lys Gly Leu Ala Trp Val Val Cys Val Tyr Gly Val Pro Leu Leu
                150                                         160
Val Val Asn Ser Phe Leu Val Leu Ile Thr Phe Leu Gln His Thr His
                            170
Pro Ala Leu Pro His Tyr Asp Ser Ser Glu Trp Asp Trp Leu Arg Gly
    180                             190
Ala Leu Ala Thr Val Asp Arg Asp Tyr Gly Ile Leu Asn Lys Val Phe
                200
His Asn Ile Thr Asp Thr Gln Val Ala His His Leu Phe Thr Met Pro
    210                             220
```

(2) INFORMATION FOR SEQ ID NO:12:

(i) SEQUENCE CHARACTERISTICS:
        (A) LENGTH:                    20 nucleotides
        (B) TYPE:                      nucleotide
        (C) STRANDEDNESS:          single
        (D) TOPOLOGY:                linear (ii) MOLECULE TYPE:           DNA (xi) SEQUENCE DESCRIPTION: SEQ ID NO:12:

GCTCTTTTGT GCGCTCATTC                                                20

(2) INFORMATION FOR SEQ ID NO:13:

(i) SEQUENCE CHARACTERISTICS:
        (A) LENGTH:                    20 nucleotides
        (B) TYPE:                      nucleotide
        (C) STRANDEDNESS:          single
        (D) TOPOLOGY:                linear (ii) MOLECULE TYPE:           DNA -continued

```
    (xi) SEQUENCE DESCRIPTION: SEQ ID NO:13:

CGGTACCAGA AAACGCCTTG                                                    20

(2) INFORMATION FOR SEQ ID NO:14:

(i) SEQUENCE CHARACTERISTICS:
         (A) LENGTH:           20 nucleotides
         (B) TYPE:             nucleotide
         (C) STRANDEDNESS:     single
         (D) TOPOLOGY:         linear (ii) MOLECULE TYPE:              DNA (xi) SEQUENCE DESCRIPTION: SEQ ID NO:14:

TAYWSNCAYM GNMGNCAYCA                                                    20

(2) INFORMATION FOR SEQ ID NO:15:

(i) SEQUENCE CHARACTERISTICS:
         (A) LENGTH:           21 nucleotides
         (B) TYPE:             nucleotide
         (C) STRANDEDNESS:     single
         (D) TOPOLOGY:         linear (ii) MOLECULE TYPE:              DNA (xi) SEQUENCE DESCRIPTION: SEQ ID NO:15:

RTGRTGNGCN ACRTGNGTRT C                                                  21
```